United States Patent
Manova-Elssibony

(10) Patent No.: US 9,728,998 B2
(45) Date of Patent: Aug. 8, 2017

(54) ENERGY HARVESTING WITH TWO CONDUCTING ANTENNA WITHIN DIFFERENT SUBSTANCES

(71) Applicant: Humavox Ltd., Kfar Saba (IL)

(72) Inventor: Asaf Manova-Elssibony, Petah-Tikva (IL)

(73) Assignee: Humavox, Ltd., Kfar Saba (IL)

( * ) Notice: Subject to any disclaimer, the term of this patent is extended or adjusted under 35 U.S.C. 154(b) by 101 days.

(21) Appl. No.: 14/377,777

(22) PCT Filed: Feb. 5, 2013

(86) PCT No.: PCT/IL2013/050106
§ 371 (c)(1),
(2) Date: Aug. 8, 2014

(87) PCT Pub. No.: WO2013/118116
PCT Pub. Date: Aug. 15, 2013

(65) Prior Publication Data
US 2016/0020631 A1   Jan. 21, 2016

Related U.S. Application Data

(60) Provisional application No. 61/596,741, filed on Feb. 9, 2012, provisional application No. 61/608,146, filed
(Continued)

(51) Int. Cl.
*H02J 7/02*       (2016.01)
*A61N 1/378*     (2006.01)
(Continued)

(52) U.S. Cl.
CPC ............ *H02J 7/025* (2013.01); *A61N 1/3785* (2013.01); *H02J 5/00* (2013.01); *H02J 17/00* (2013.01);
(Continued)

(58) Field of Classification Search
CPC .... H02J 7/02; H02J 7/025; H02J 5/005; H02J 17/00; H02J 5/00; B60L 11/1824;
(Continued)

(56) References Cited

U.S. PATENT DOCUMENTS 6,975,280 B2 * 12/2005 Jenwatanavet ........ H01Q 5/357
343/702
2006/0025897 A1 * 2/2006 Shostak ................ B60C 23/005
701/1
(Continued)

FOREIGN PATENT DOCUMENTS

DE        10256099 A1   6/2004
EP         1437816 A2   7/2004
(Continued)

OTHER PUBLICATIONS

International Search Report Issued in PCT/IL2013/050106 dated Nov. 21, 2013.

*Primary Examiner* — Richard Isla Rodas
*Assistant Examiner* — Dung V Bui
(74) *Attorney, Agent, or Firm* — Maxwell L. Minch; GrayRobinson, P.A.

(57) ABSTRACT

A system is presented for harvesting electromagnetic energy propagating in surroundings. The system comprises an antenna unit, a harvesting unit, and an input signal adapting circuit. The antenna unit is configured for receiving external electromagnetic radiation from the surroundings and producing a corresponding electric output. The harvesting unit comprises at least one energy harvesting circuit each configured and operable for receiving signals indicative of the output of the antenna unit and generating and storing corresponding electric charge, the harvesting circuit comprising: a rectifying unit comprising a plurality of rectifiers each configured and operable to receive AC electric signals and generate corresponding DC electric power; and a charge
(Continued)

collection unit configured and operable to receive the plurality of DC electric powers from said rectifying unit and converting and accumulating them into the electric charge presenting harvested energy. The input signal adapting circuit has an input connected to the antenna unit and an output connected to the rectifying unit, the input signal adapting circuit being configured and operable for adjusting a predetermined electrical property of the antenna unit and rectifying unit to thereby optimize receipt of the electric output of the antenna unit to the harvesting circuit.

8 Claims, 13 Drawing Sheets

Related U.S. Application Data on Mar. 8, 2012, provisional application No. 61/607,679, filed on Mar. 7, 2012, provisional application No. 61/641,262, filed on May 1, 2012.

(51) Int. Cl.
  *H02J 5/00* (2016.01)
  *H03H 7/01* (2006.01)
  *H02J 17/00* (2006.01)
  *H03H 7/38* (2006.01)
  *H02J 50/20* (2016.01)
  *H02J 50/27* (2016.01)

(52) U.S. Cl.
  CPC .............. *H02J 50/20* (2016.02); *H02J 50/27* (2016.02); *H03H 7/0138* (2013.01); *H03H 7/38* (2013.01)

(58) Field of Classification Search
  CPC ... B60L 11/1833; B60L 11/1846; H03H 7/38; H03H 7/0138; H03H 7/01; A61N 1/3785; A61N 1/378
  USPC .................................................. 320/107, 109
  See application file for complete search history.

(56) References Cited

U.S. PATENT DOCUMENTS

| | | |
|---|---|---|
| 2007/0010295 A1 | 1/2007 | Greene et al. |
| 2007/0153561 A1 | 7/2007 | Mickle et al. |
| 2008/0306359 A1* | 12/2008 | Zdeblick .............. A61B 5/0028 600/302 |
| 2009/0067208 A1 | 3/2009 | Martin et al. |
| 2010/0039234 A1* | 2/2010 | Soliven ..................... H04B 5/02 340/10.1 |
| 2011/0160802 A1* | 6/2011 | Rofougaran .......... G06F 19/323 607/60 |
| 2011/0163857 A1* | 7/2011 | August .............. G06K 19/0723 340/10.42 |
| 2011/0163882 A1* | 7/2011 | August ................ A01K 11/004 340/573.1 |
| 2011/0181422 A1* | 7/2011 | Tran .................... G06F 19/3418 340/573.1 |
| 2011/0309686 A1 | 12/2011 | Scherbenski et al. |

FOREIGN PATENT DOCUMENTS

| | | |
|---|---|---|
| WO | WO-2006121835 A1 | 11/2006 |
| WO | WO-2007146164 A2 | 12/2007 |

* cited by examiner

ENERGY HARVESTING WITH TWO CONDUCTING ANTENNA WITHIN DIFFERENT SUBSTANCES

CROSS-REFERENCE TO RELATED APPLICATIONS

This application is a U.S. National Phase application under 37 U.S.C §371 of Patent Cooperation Treaty Application No. PCT/IL2013/050106, filed on Feb. 5, 2013, entitled Energy Harvesting System, which claims priority to U.S. Provisional App. No. 61/596,741, filed Feb. 9, 2012, U.S. Provisional App. No. 61/607,679, filed Mar. 7, 2012, U.S. Provisional App. No. 61/608,146, filed Mar. 8, 2012 and U.S. Provisional App. No. 61/641,262, filed May 1, 2012, the contents of which are incorporated by reference herein.

TECHNOLOGICAL FIELD AND BACKGROUND

The present invention is in the field of energy harvesting techniques and relates to an energy harvesting system which may be useful in various applications including medical devices (e.g. implantable devices), as well as electric vehicles, and various domestic devices.

In the last two decades, the usage of electromagnetic communication, such as RF communication, has dramatically increased in all aspects of human life, including mobile/satellite communication, medical treatments, and the like, while different parts of the radio frequency spectrum can be used for different radio transmission technologies and applications (e.g., as TV (television) or cellular applications). Generally, the radio frequency spectrum is shared by civil, government, and military users of all nations, according to International Telecommunications Union (ITU) radio regulations. Thus, people all over the world are surrounded by a variety of electromagnetic signals (radiation), which propagate in the air and have different frequencies and strength.

There have been several attempts in the art to collect electromagnetic signals which propagate in the air, and to generate electrical power. Some techniques of the kind specified are described for example in the following patents: EP 1,722,284, US 2009/105,782, and JP 10146077.

In recent years, there has been a rapid technological advance in medical implanted and attached devices. However, the majority of these devices, if not all, require electricity as their energy source. Each such medical device uses batteries as a disposable electricity source. When it comes to implanted devices such as a heart pace maker or a defibrillator, a change of a battery per se requires repetitive surgeries that endanger the patient and expose him to various risks along with the fears before a surgery, inconvenient of the procedure, and recovery period that comes after. When it comes to attached devices such as a hearing aid, the change of batteries that may vary from once a day to once a week according to the device type is merely a nuisance.

Thus, it is obvious that a mechanism, capable of charging a battery and possibly eliminating a need for battery in such devices, is desired.

GENERAL DESCRIPTION

There is a need in the art in a novel approach for energy harvesting enabling efficient collection and use of electromagnetic radiation (e.g., RF signals) and storage of the harvested energy in order to be supplied to an electrical load, such as a rechargeable battery or an electric device to enable for example, charging said battery or operating said electric device, in a most efficient manner. A technique for harvesting electromagnetic energy is described in U.S. patent application Ser. No. 13/116,554 of the same inventor incorporated herein in its entirety by reference. Such system functionally allows gathering the already existing RF radiation from the surrounding and converting it into usable energy source.

The present invention provides a novel energy harvesting system and method, as well as a novel antenna unit for use in an energy harvesting system. The antenna unit of the invention is configured for receiving external electromagnetic radiation from the surroundings and producing a corresponding output electric signal. The antenna unit comprises at least two electrically conductive elements associated with (e.g. positioned in) different transmission media having different electric and/or magnetic properties.

When harvesting RF energy from sources available in the air, the efficiency of the system is of critical importance due to the variety of frequencies and intensities of received signals. One of important factors determining the efficiency of a harvesting system is a degree of match/adjustment of a predetermined electrical property of the antenna unit and that of the rectifying unit. More specifically, this may be a match between the impedance of a rectifying circuit and the intensity of an input signal. The rectifier impedance is dynamically changing as a function of the intensity of the input signal. More specifically, when the input signal is a low power signal relative to the conductive threshold of the rectifier, the impedance of the rectifier is very high. As the intensity of the input signal increases and approaches the conductive threshold of the rectifier, the impedance of the rectifier decreases, until the intensity of the signal exceeds the conductive threshold of the rectifier and the impedance of the rectifier decreases. In a static system, the rectifier is configured such that it impedance matches a certain level of intensity of an input signal, but in other intensities it is not matched and the efficiency decreases significantly. Thus, there might be a need for an input signal adapting unit/circuit, e.g. an adaptive impedance matching unit, that is configured and operable for dynamically/selectively matching the rectifier impedance according to the changing input signal intensity to the impedance of the antenna unit.

One way of fulfilling a requirement for a dynamic change of impedance of the rectifier is by providing a dynamic active change of the input impedance. This technique however suffers from energy consumption leading to energy waste.

It is thus desired in some applications that such a dynamic impedance matching would be implemented by a passive unit. In this connection, it should be understood that the terms "passive unit" and "active unit" used herein refer to units/circuits which are, respectively, autonomously operable based on their predefined working parameters/conditions and operable by a dedicated controller to vary one or more of the working parameters/conditions. The invention provides such a passive filtering unit that operates to match the impedances of the rectifiers of different input intensity signals (received from the antenna unit) and maximize the efficiency of the harvesting system in all input intensity levels.

When harvesting electromagnetic energy, a capacitor of each rectifier is usually small. However, there is a need for storage of large quantities of charge originated from several rectifiers and from the same rectifier over time. The present invention provides a novel charge collection unit which may be based on either one of the two following novel approaches for gathering the small charges obtained during the harvesting process into a large storage (i.e. capacitor with relatively large capacitance). This is implemented in the invention either by using a switching topology circuit or by using appropriate conversion of voltage to current allowing transferring the small charges obtained to a large capacitor to enable large electric charge storage. To this end, the invention provides a charge collection unit comprising a signal summing unit which is configured and operable to receive a plurality of DC electric powers from multiple rectifiers of a rectifying unit and convert and accumulate them into the electric charge (via a voltage to current conversion or a switching topology circuit), where this charges presents the harvested energy.

Thus, according to one broad aspect of the present invention, there is provided a system for harvesting electromagnetic energy propagating in the surroundings to which the system is exposed. The system comprises: an antenna unit configured for receiving external electromagnetic radiation from the surroundings and producing a corresponding electric output; a harvesting unit comprising one or more harvesting circuits wherein each harvesting circuit is configured and operable for receiving signals indicative of the output of the antenna unit and generating and storing corresponding electric charge presenting the harvested energy; and an input signal adapting circuit which has an input connected to the antenna unit and an output connected to said at least one harvesting circuit of the harvesting unit and is operable for adjusting a predetermined electrical property of the antenna unit and said at least one harvesting circuit to thereby optimize receipt of the electric output of the antenna unit by said at least one harvesting circuit.

It should be noted that in this disclosure terms "unit" and "circuit" are used interchangeably because each of them actually refers to one or more electric circuits defining certain functionality for affecting/processing an electric input.

The harvesting circuit comprises a rectifying unit comprising a plurality of rectifiers each configured and operable to receive AC electric signals and generate corresponding DC electric power; and a charge collection unit configured and operable to receive the plurality of DC electric powers from said rectifying unit and converting and accumulating them into the electric charge presenting harvested energy.

Generally, the antenna unit may be of any known suitable configuration. Preferably, however, a novel antenna structure of the invention can be used. Such novel antenna structure comprises at least two electrically conductive elements associated with different transmission media differing in at least one of electric and magnetic properties. It should be understood that such a structure is termed herein as "antenna unit" solely in the meaning that it is responsive to electromagnetic radiation to which the structure is exposed (typically RF radiation) and providing a corresponding electric output (response signal).

In some embodiments, such at least two different transmission media may for example include at least two different animate tissues (in which case the antenna unit may be implanted in a subject); or may include animate tissue and air (in which case the antenna unit is attached to a subject). It should, however, be understood that the antenna unit of the invention is not limited to these examples, as well as is not limited to any specific media.

The input signal adapting unit is configured and operable to optimize receipt of the antenna output to the rectifying unit of the harvesting circuit by matching between the electric parameter, e.g. impedance, of the antenna unit and the rectifying unit.

In some embodiments, the input signal adapting unit comprises an impedance matching unit and a filtering unit connected to the impedance matching unit. The impedance matching unit is configured to match between the impedances of the antenna unit and the filtering unit. The filtering unit is configured and operable for sorting the received RF band propagating in the surroundings into a predefined number of subbands with predetermined values of central frequency, band width and strength for each subband. The predefined number of subbands corresponds to a number of the rectifiers in the rectifying unit.

In some embodiments, the input signal adjusting unit comprises an adaptive impedance matching unit, and a control unit connectable to the adaptive impedance matching unit and configured and operable operation thereof. The adaptive impedance matching unit is configured and operable to controllably adjust impedance of the rectifiers of the rectifying unit to signal intensities of multiple frequency bands received by the antenna unit.

In some embodiments, the charge collection unit comprises a signal summing unit comprising a switching topology circuit and a controller. The switching topology circuit comprises a predetermined number of capacitors corresponding to a number of the rectifiers in the rectifying unit, all electrically connected to a storage capacitor. The capacitors connected to output of the respective rectifiers have relatively small capacitance values, while the storage capacitor has a relatively large capacitance value. The switching topology circuit is adapted to controllably switch between the plurality of DC signals received from the plurality of rectifiers respectively with the corresponding plurality of the "small" capacitors for power summation and storage of corresponding charge on the "large" capacitor.

In some embodiments, the charge collection unit comprises a signal summing unit comprising a voltage to current unit. The voltage to current unit comprises a predetermined number of voltage to current conversion circuits having inputs connected to the outputs of the corresponding number of the rectifiers respectively, and having outputs connected to a storage a capacitor. The voltage to current unit is thereby adapted to convert and sum the plurality of DC signals/powers received from the plurality of rectifiers via the plurality of voltage to current conversion circuits.

The system may further comprise a control unit connected to at least one of the input signal adapting unit (e.g. impedance matching unit) and the charge collection unit. Considering the control unit is connected to at least the charge collection unit comprising a switching topology circuit described above, the control unit operates the switching topology to controllably switch between the plurality of DC signals received from the plurality of rectifiers respectively with the corresponding plurality of "small" capacitors of the relatively small capacitance values for power summation and storage of corresponding charge on the "large" capacitor.

It should be noted that the same input signal adapting unit may be associated with multiple harvesting circuits. Also, the same charge collection unit may be associated with multiple harvesting circuits by adjusting the number of inputs of the charge collection unit to the total number of rectifiers defined by the multiple harvesting circuits.

The harvesting unit may comprise a connection port for connecting output of the charge collection unit (defined by charge storage utility in the form of a large capacitor) to at least one electrical load. The at least one electrical load may include at least one of the following: a rechargeable battery, a medical device, an electric vehicle component, an electric device for home use. The medical device may include at least one of the following: a pacemaker, a defibrillator, and a hearing aid. The electric vehicle component may include at least one of the following: electrical accessories, audio systems and amplifiers, TV and DVD systems, GPS systems, air conditioning systems, alarm systems, lights and wiring systems.

In accordance with another broad aspect of the invention there is provided an antenna unit configured and operable for receiving external electromagnetic radiation from surrounding and producing a corresponding output electric signal. The antenna unit comprises at least two conductive elements positioned in at least two different transmission media being different in electric and/or magnetic properties. The received external electromagnetic radiation creates a potential difference between the at least two conductive elements producing an output electric signal, thereby allowing uptake of the external electromagnetic radiation from the surroundings.

As mentioned above, in some specific but not limiting examples, the different transmission media may include different animate tissues; or animate tissue and air.

In accordance with yet another broad aspect of the present invention, there is provided an input signal adapting unit for use with an antenna exposed to electromagnetic radiation of RF band propagating in surroundings. The input signal adapting unit comprises an impedance matching unit and a filtering unit connected to the impedance matching unit. The impedance matching unit is configured and operable to match between impedances of the antenna unit and the filtering unit, and the filtering unit is adapted for sorting the RF band into a predefined number of subbands of a predetermined frequency, bandwidth and strength for each subband.

The present invention in its further broad aspect is directed to a charge collection unit comprising a signal summing unit adapted to receive a plurality of DC electric signals and sum them in the form of an electric charge on a storage capacitor, the signal summing unit comprising at least one of a switching topology unit and a voltage to current unit.

The switching topology unit may comprise a predetermined number of capacitors having relatively small capacitance values and being connectable to output of a corresponding number of rectifiers respectively, and connected to said storage capacitor of a relatively large capacitance value. The switching topology unit is adapted to controllably switch between DC sources received from the rectifiers with the predetermined number of the capacitors for power summation.

The voltage to current unit may comprise a predetermined number of voltage to current conversion circuits having inputs connectable to outputs of a corresponding number of rectifiers respectively, and outputs connected to the storage capacitor. The voltage to current unit is thereby configured and operable to convert and sum a plurality of DC sources received from the plurality of rectifiers via the voltage to current conversion circuits.

BRIEF DESCRIPTION OF THE DRAWINGS

Examples illustrative of variations of the disclosure are described below with reference to figures attached hereto. In the figures, identical structures, elements or parts that appear in more than one figure are generally labeled with the same numeral in all the figures in which they appear. Dimensions of components and features shown in the figures are generally chosen for convenience and clarity of presentation and are not necessarily shown to scale. The figures presented are in the form of schematic illustrations and, as such, certain elements may be drawn greatly simplified or not-to-scale, for illustrative clarity. The figures are not intended to be production drawings.

The figures (Figs.) are listed below.

FIGS. 1C and 1D illustrate two examples of the system utilizing semi-active mode of the operation mode of major components of the system.

DETAILED DESCRIPTION OF THE EMBODIMENTS

Figure 1A:
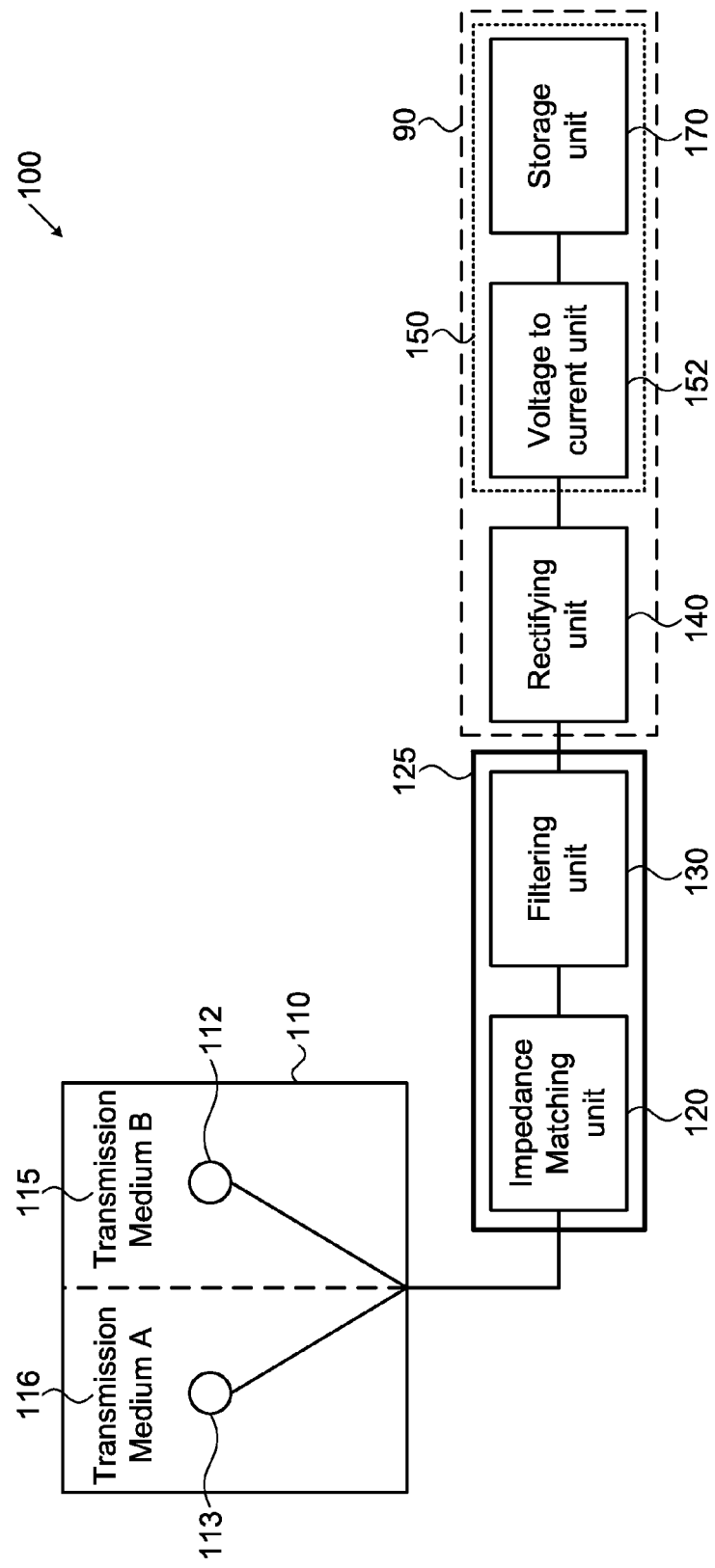
FIG. 1A-1D are block diagrams schematically illustrating several examples of the configuration of an energy harvesting system of the present invention; wherein in the example of FIG. 1A the operation mode of major components of the system is a passive mode that do not require additional adaptations for obtaining proper operation of the harvesting system; in the example of FIG. 1B the operation mode of major components of the system is an active mode that requires adjustment of the operation of specific units of the system to a current condition of the harvesting process.

Although various features of the disclosure may be described in the context of a single embodiment, the features may also be provided separately or in any suitable combination. Conversely, although the disclosure may be described herein in the context of separate embodiments for clarity, the disclosure may also be implemented in a single embodiment. Furthermore, it should be understood that the disclosure can be carried out or practiced in various ways, and that the disclosure can be implemented in embodiments other than the exemplary ones described herein below. The descriptions, examples and materials presented in the description, as well as in the claims, should not be construed as limiting, but rather as illustrative.

Reference is made to FIGS. 1A-1D which show, by way of block diagrams, several embodiments of the configuration of an energy harvesting system of the present invention. The system includes such main constructional parts as an antenna unit 110, and an energy harvesting unit 90 including one or more harvesting circuits each receiving and processing an output of the antenna unit 110; and an input signal adapting unit 125. The harvesting circuits includes a rectifying unit 140, and a charge collection arrangement 150 which either includes a storage capacitor, or is connected to a separate storage unit 170 having such storage capacitor, for accumulating charge presenting harvested energy.

FIG. 1A illustrates the energy harvesting system configuration 100, in which the operation mode of major components is a passive mode, i.e. the mode that doesn't require additional adaptations for obtaining proper operation of the harvesting system. The system 100 includes the antenna unit 110, the energy harvesting unit 90, and the input signal adapting unit 125. The harvesting unit 90 includes the rectifying unit 140, and the charge collection arrangement 150. In this example, the input signal adapting unit 125 includes an impedance matching unit 120 and a filtering unit 130 the operation of which will be described below. Also, in this example, the charge collection arrangement 150 includes a voltage to current converter 152, as will be described more specifically further below.

Generally, the antenna unit may be of any known suitable kind. Preferably, the antenna unit 110 used in the system 100 utilizes the novel antenna configuration of the present invention. The antenna unit 110 of this novel configuration includes at least two electric conductors (conductive elements) 112 and 113, which are positioned in at least two different substances constituting transmission media 115 and 116, having different electrical and/or magnetic properties. Due to the different electrical and/or magnetic properties of substances 115 and 116, RF radiation in the surrounding of the antenna unit creates different electric potentials on the conductive elements 112 and 113. The potential difference between the two conductive elements is received by the harvesting unit 90 via the harvesting circuit and is then processed by the input adapting unit 125. To this end, the signal undergoes impedance matching by unit 120 and filtering by unit 130 that operate together to adjust the impedance of antenna unit 110 to the impedance of the rectifying unit 140 to thereby allow optimal delivery of the received signal.

Generally, impedance matching unit 120 is used to enable transferring maximal electromagnetic energy/power from the antenna unit to the harvesting unit. In the configuration illustrated in this figure, the impedance of antenna unit 110 includes both the impedances of the transmitting media and the conductive elements that transfer the received energy into the harvesting unit. In order to transfer maximal electromagnetic power from the antenna into the harvesting unit, the impedance of the antenna, $Z_{Antenna}$, needs to be equal (generally as close as possible) to the complex conjugate of the harvesting unit impedance, $Z^*_{Harvesting\ unit}$, namely the following condition is to be satisfied:

$$Z_{Antenna} = Z^*_{Harvesting\ unit}$$

Impedance matching unit 120 may comprise appropriate electrical circuits which may contain a combination of capacitive elements and inductive elements. Generally, the impedance matching unit 120 may be of any suitable configuration known in the art.

The received signals are then delivered to the filtering unit 130. Filtering unit 130 is configured and operable as a spectral filter and includes one or more arrays/sets of filters which sorts/divides the signals received from antenna unit 110 to predefined frequency bands. The spectral filtering process in accordance with the present invention is a non active process, in the meaning that is mainly directed to sort different signal frequencies that are characterized by having different strengths. A specific but not limiting example of a filtering unit is described in details further below with reference to FIG. 5. The output of each of the last filters in the sets/arrays of filters is connectable to a dedicated rectifier in the plurality of rectifiers comprised in the rectifying unit 140. The rectifier is configured to convert the respective filtered RF signal into a DC signal according to pre-expected signal strength, thus, eliminating the need for active matching process that usually consumes energy.

The rectifying unit 140 includes an array of rectifiers associated with a signal summing utility of the charge collection unit. The output of each rectifier is connected to such a signal summing utility that is adapted to receive plurality of DC electric signals, and perform their summation so as to allow storage thereof in a storage capacitor/unit 170.

In this specific but not limiting example of FIG. 1A, the output of each rectifier in the rectifying unit 140 is connected to the respective voltage to current conversion circuit in the voltage to current unit 152. Voltage to current convertor unit 152 is configured and operable for summing several DC sources into one storage unit 170. It should be noted that the voltage to current unit 152 is preferably configured to allow for passively accumulating several DC sources into the common storage without the need for active operations and without causing shortcuts and/or other interfering influences between the summed DC sources as normally occurs while connecting directly several DC voltage sources, as will be described in details hereinafter with reference to FIG. 11. The storage unit 170 is configured to collect the entire harvested energy, and it may be further connected to one or more electrical loads (not shown) such as a rechargeable battery or an electric device.

Figure 1B:
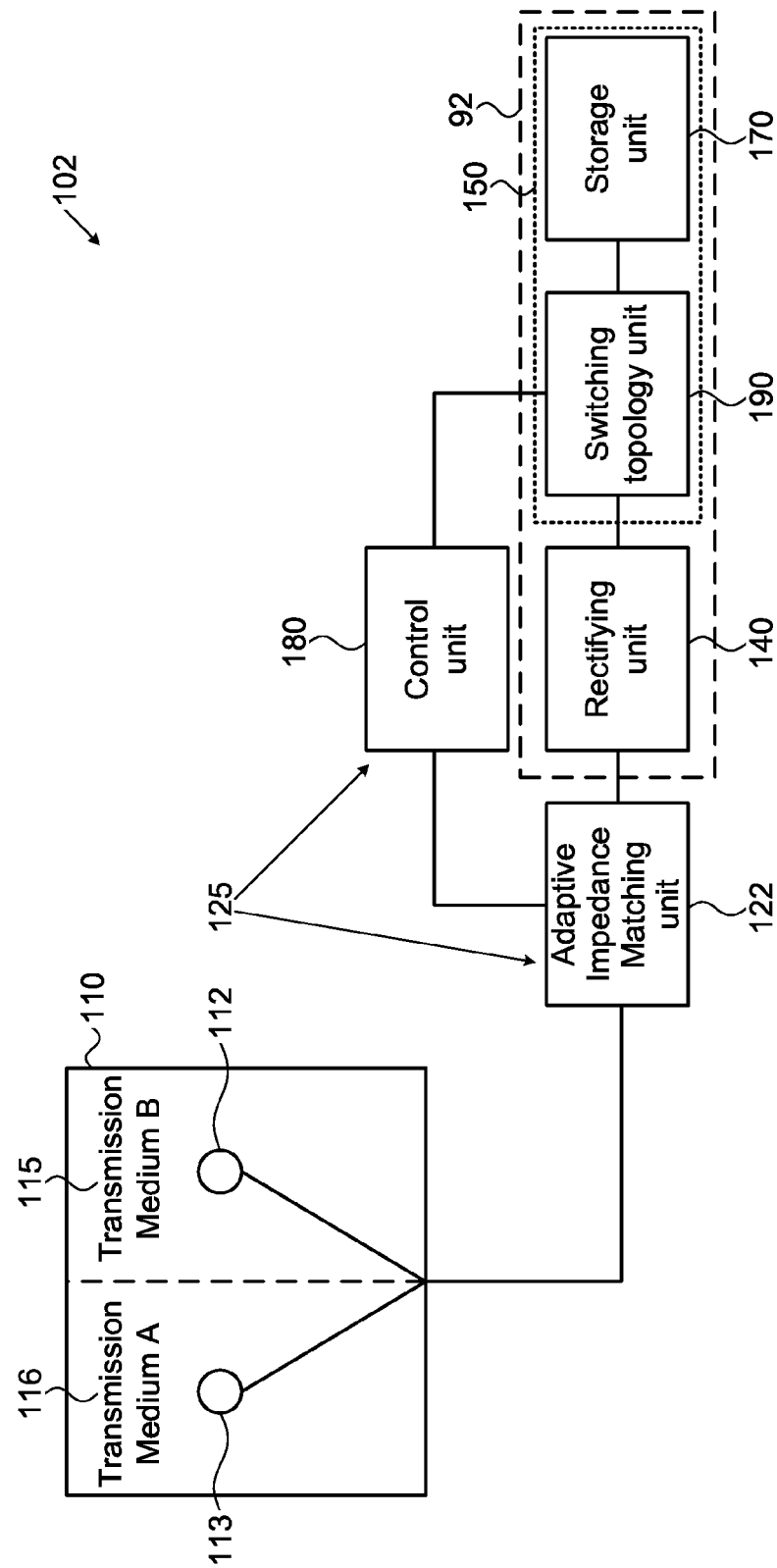

FIG. 1B illustrates another example of the energy harvesting system configuration 102 in which the operation mode of major components is an active mode that requires a control unit for adjusting the operation of specific units of the system to a current condition of the harvesting process. The system 102 is configured generally similar to the above described system 100 in that it comprises an antenna unit 110 which is preferably configured according to the invention, namely includes two conductors 112 and 113 positioned in different transmission media 115 and 116, and comprises a harvesting unit 92 and an input signal adapting unit 125. The harvesting unit 92, similar to the above-described example includes, a rectifying unit 140, and a charge collection arrangement 150. In this example, the input signal adapting unit 125 includes an adaptive impedance matching unit 122 and a control utility 180. The adaptive impedance matching unit 122 is configured to adjust the impedance of antenna unit 110 to the impedance of the rectifying unit 140 to thereby allow optimal delivery of the received signal.

Generally, in order to harvest energy from electromagnetic waves there is a need to rectify the harvested energy that is received from the antenna unit to thereby receive a DC electrical energy that can be reused as an energy source. The input characteristic impedance of the rectifying unit is not stable and can be varied from some Ohms to Mega Ohms as a function of the input RF level on the rectifier input. In addition, the antenna unit characteristic impedance can be stable or unstable. One technique that allows for adapting stable or unstable antenna to an unstable input impedance front end circuit is an adaptive impedance matching technique.

Adaptive impedance matching unit 122 is configured and operable by the control unit 180 to constantly adapt the antenna impedance into an unstable characteristic impedance of the harvesting circuit. To this end, the control unit 180 operates to control the parameters of the impedance matching unit to match the impedance of the rectifier to that of the antenna unit. The control unit 180 is operable to vary the impedance of the impedance matching unit 122 in accordance with the input voltage on the harvesting circuit. The control unit 180 is configured and operable to maximize the efficiency of the electrical system by varying the impedance of the impedance matching unit 122 in accordance with electrical characteristics measured in predetermined locations along the circuit. The control unit 180 operates to vary at least one of input and output impedance values of the impedance matching unit to maximize the voltage in predetermined locations. The control unit may be an electronic unit preferably configured of linear electronic elements or a software utility operating on an electronic device. The control unit has at least two input ports for detecting electrical parameters at said predetermined locations, a comparator module for comparing the detected parameters, and at least one output port for providing a control signal to the impedance matching unit to thereby vary its impedance. In the specific example illustrated in FIG. 1B, the control unit 180 is adapted to control the adaptation of the impedance according to the strength of the signal received.

The received signal is then delivered to a rectifier in the rectifying unit 140 that is adjusted to convert the RF signal into a DC signal. The output of each rectifier of the rectifying unit 140 is connected to the charge collection arrangement 150. In the example of FIG. 1B, the charge collection arrangement 150 includes a switching topology unit 190 and a control utility and is configured and operable to allow summing several DC sources into one storage capacitor unit 170. The control utility of the charge collection arrangement 150 and that of the input signal adapting unit 125 may be incorporated in separated controllers or may be parts of the same control unit 180. The switching topology unit 190 includes several switching circuits, the operation of which is controlled by the respective control utility (e.g. in the control unit 180). A detailed description of an example of the switching topology unit is described below with reference to FIG. 6-10. The storage unit 170 collects the entire harvested energy, and as mentioned above may further be connected to a rechargeable battery or to an electrical device.

Figure 1C:
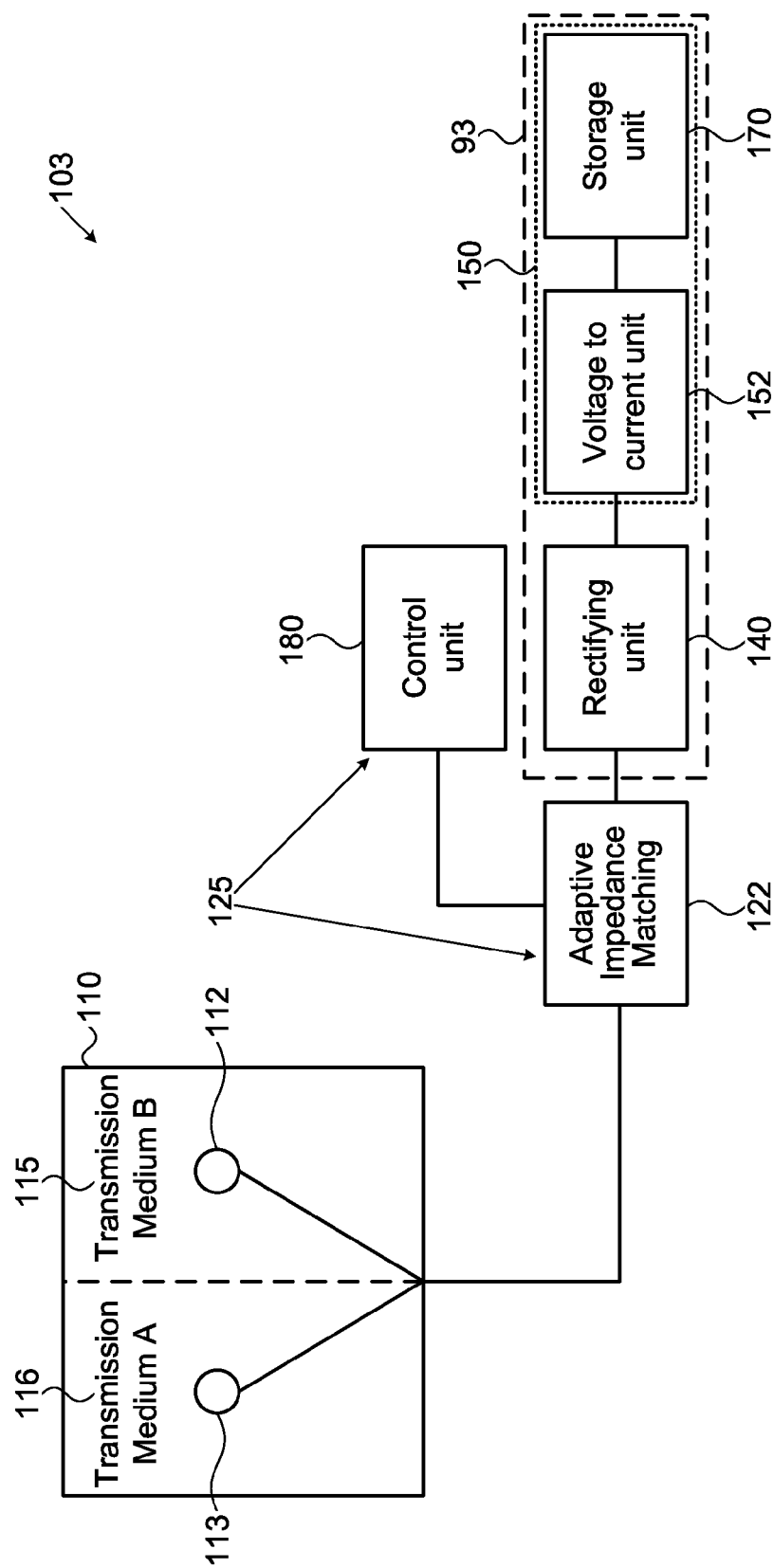

FIG. 1C exemplifies a harvesting system 103 in which the operation mode of major components is a semi-active mode that requires a control unit for adjusting the operation of the system to the current stage of the harvesting process. The system 103 is configured generally similar to the above described systems 100 and 102 comprising an antenna unit 110 preferably including two conductors 112 and 113 positioned in different transmission media 115 and 116, a harvesting unit 93 and an input signal adapting unit 125. The harvesting unit 93 has at least one harvesting circuit for receiving the RF output of the antenna unit. The harvesting unit 93 each harvesting circuit thereof, similar to the above-described examples, includes a rectifying unit 140, and a charge collection arrangement 150 including or connected to an energy storage capacitor unit 170. The system 103 is similar to the above-described unit 102 (FIG. 1B) in that input signal adapting unit 125 includes an adaptive impedance matching unit 122 and a control utility constituted by a control unit 180. The adaptive impedance matching unit 122 is configured and controlled by the control unit 180 to adjust the impedance of the antenna unit 110 to the impedance of the harvesting unit 93 (rectifying unit) to thereby allow optimal delivery of the received signal, e.g. by controlling the adaptation of the impedance according to the strength of the signal received. The harvesting unit 93 is similar to the above-described unit 90 (FIG. 1A) in that its charge collection arrangement 150 is configured as a voltage to current convertor. Thus, the received antenna signal is delivered to a rectifier in the rectifying unit 140 that is adjusted to convert the RF signal into a DC signal. The output of each rectifier is connected to the voltage to current unit 152 which allows summing several DC sources into one storage unit 170 configured to collect the entire harvested energy. As indicated above, the storage unit may further be connected to a rechargeable battery or to an electrical device (not shown).

Figure 1D:
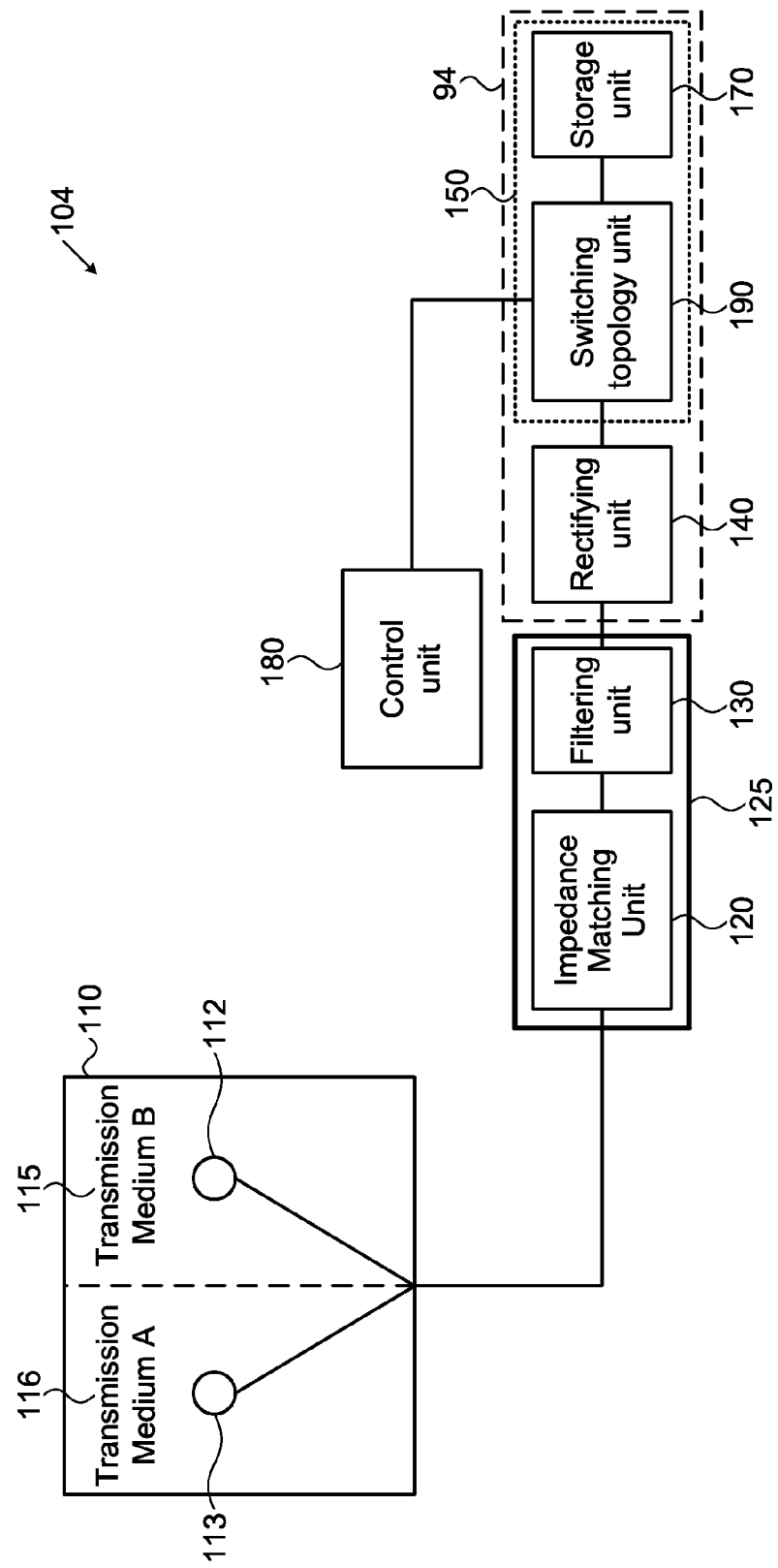

FIG. 1D illustrates yet another example of an energy harvesting system 104 utilizing a semi-active mode of operation of the major components of the system. The system 103 is configured generally similar to the above described systems 100, 102 and 103 comprising an antenna unit 110 preferably including two conductors 112 and 113 positioned in different transmission media 115 and 116, a harvesting unit 94 having at least one harvesting circuit for receiving the RF output of the antenna unit, and an input signal adapting unit 125. The harvesting unit 94 (each harvesting circuit thereof), similar to the above-described examples, includes a rectifying unit 140, and a charge collection arrangement 150 including or connected to an energy storage capacitor unit 170. The system 104 is similar to the above-described unit 100 (FIG. 1A) in that its input signal adapting unit 125 includes an impedance matching unit 120 and a filtering unit 130 that are configured to adjust the impedance of antenna unit 110 to the impedance of rectifying unit 140 to thereby allow optimal delivery of the received signal. The harvesting unit 94 is similar to the above-described unit 92 (FIG. 1B) in that its charge collection arrangement 150 includes a switching topology unit 190 and a control utility constituted by a control unit 180 and is configured and operable to allow summing several DC sources into one storage unit 170.

The received signal is delivered to a rectifier comprised in rectifying unit 140 that is adjusted to convert the RF signal into a DC signal. In accordance with the variation illustrated in this figure, the output of each rectifier of rectifying unit 140 is functionally connected to the switching topology circuit in switching topology unit 190 that allows summing several DC sources into one storage capacitor unit 170. The switches position for charging/discharging configuration is determined by control unit 180.

It should be noted that the principles of the present invention are not limited to any specific configuration of any one of the above mentioned units and any known suitable configuration can be used in the system of the invention as any men skilled in the art may configure, provided these units have the above described functional features for implementing the technique of the invention. In addition, the harvesting system provided herein may comprise off the shelf antenna, while preferably at least two antenna elements are positioned in different substance (transmission media). As described above, such antenna unit of the present invention provides maximal gain enhancement due to different transmission media surrounding the conductive elements that functionally create an antenna effect that allows uptake of electromagnetic radiation from the surroundings.

The conductive elements are inserted or attached to at least two different transmission media with different electrical and/or magnetic properties (e.g. permeability, permittivity, and conductivity) in order to increase the antenna maximal gain to functionally allow better performance of the antenna. In some applications of the invention, at least one conductive element of such novel antenna unit is positioned in contact with a user's body. The different transmission media can thus be, but not limited to, skin and air if the antenna is attached to a body or it can be, but not limited to, two different tissue types such as muscle and fat, muscle and intracellular fluid, muscle and fat tissue, dermis and fat tissue, and any other combination thereof, when the antenna is implanted in a body. The novel antenna may also be applicable for uses outside animate bodies, as long as the conductive elements are positioned in at least two different substances that differ from each other in their electrical and/or magnetic properties.

The general theory of electromagnetic phenomena is based on Maxwell's equations, which constitute a set of four coupled first-order partial-differential equations resulting the space and time changes of electric and magnetic fields to their scalar source densities (divergence) and vector source densities (curl). For stationary media, Maxwell's equations in the differential form are:

$$\nabla \cdot D(r,t) = \rho(r,t) \quad \text{(Gauss's electric law)} \tag{1}$$

$$\nabla \cdot B(r,t) = 0 \quad \text{(Gauss's magnetic law)} \tag{2}$$

$$\nabla \times E(r,t) = -\partial B(r,t)/\partial t \quad \text{(Faraday's law)} \tag{3}$$

$$\nabla \times H(r,t) = \partial D(r,t)/\partial t + J(r,t) \quad \text{(Ampere's law)} \tag{4}$$

wherein E is the electric field intensity [volt/meter]; H is the magnetic field intensity [Ampere/meter]; D is the electric flux density [Coulomb/square meter]; B is the magnetic flux density [Tesla or Weber/square meter]; ρ is the free electric charge density [Coulomb/cubic meter]; and J is the free electric current density [Ampere/square meter].

Maxwell's equations involve only macroscopic electromagnetic fields and, explicitly, only macroscopic densities of free charge ρ(r,t) giving rise to the free current density J(r,t). The effect of the macroscopic charges and current densities bounded to the medium's molecules is indicated by auxiliary magnitudes D and H, which are related to the electric and magnetic fields E and H by the so-called constitutive equations that describe the behavior of the medium. In general, the quantities in these equations are functions of the position (r) and the time (t).

The power density that the electromagnetic field carries in the free space is defined by Poynting's vector:

$$S = E \times H \quad \text{[Watt/square meter]} \tag{5}$$

which represents the power passing through a unit area perpendicular to the propagation vector r. Inside matter, the power density $S_v$ [Watt/cubic meter] is related to the work (or heat) supplied to the charge distribution:

$$S_v = dS/dv = E \cdot J \tag{6}$$

known as the point form of Joule's law.

Inside matter, additional physical quantities are introduced to describe the interaction of waves with molecules. The electric permittivity $\in$ is connected to the electric field and to the electric flux, but also to a new macroscopic vector P [Coulomb/square meter] called the electric polarization vector, such as:

$$D = \in E + P \tag{7}$$

For most materials, being linear isotropic media, especially the human body tissues, the macroscopic vector P can be considered as co-linear and perpendicular to the applied electric field. Thus, we get:

$$P = \in \chi_e E \tag{8}$$

wherein $\chi_e$ is the electric susceptibility of the matter (i.e. capability of the matter to be polarized) and D can be written as:

$$D = \in_o \in_r E \tag{9}$$

The magnetic behavior in matter involves a similar treatment with the following relations:

$$H = B/\mu - M \tag{10}$$

$$M = \chi_m H \tag{11}$$

$$B = \mu_o \mu_r H \tag{12}$$

wherein μ is the magnetic permeability and $\chi_m$ is the magnetic susceptibility. Since the human body has very minor magnetic effects we neglect here the magnetic nature of the tissues and consider only their electric nature. Very often the relation between the electric field E and the current density J is given at any specific point by Ohm's law:

$$J(r,t) = \sigma E(r,t) \tag{13}$$

wherein σ [mho/meter] is the conductivity of the matter.

Now the configuration of electromagnetic waves is considered in the boundaries between air ("transmission medium A") and matter ("transmission medium B"). In free space, the existing fields are pure electric field E and magnetic field H and the power density obeys Poynting's law with $\in_r = 1$ and $\mu_r = 1$. In the human body, the fields are presented by the electric flux density D and magnetic field intensity H (because in case of no magnetic effects B=H), and the local parameters are electric permittivity $\in$ (actually a complex number written as ($\in_o$ ($\in'$+j$\in''$))) and conductivity of the matter σ.

When a plane wave propagating in free space interacts with the human body, part of the energy of the wave is reflected back to air and part of the energy penetrates into the body. From the penetrating part, some portion continues to propagate inside the body and some portion is absorbed by the tissues and bones. The absorbed power can be summed as the integral of many local interactions:

$$S(\text{absorbed}) = 0.5 \int P v \, dv = 0.5 \int (E \cdot J) \, dv = 0.5 \int \sigma |E|^2 \, dv \tag{14}$$

The factor of 0.5 is indicative of that the dissipation is related to average power and not to the peak power. The absorbed power in the human body is often expressed by the term SAR (Specific Absorption Rate) which is no other than:

$$\text{SAR} = (\sigma/2\rho)|E|^2 \tag{15}$$

wherein σ is the conductivity [mho/meter] in any specified area and p is the mass density [kg/cubic meter] in any specified area. The units of the SAR quantity are therefore [Watt/kg]. SAR is the most commonly used indicator and measure for safety standards in RF exposure.

The next table exemplifies the tissues dielectric constant and conductivity for several tissues at 900 MHz:

| Tissue | $\epsilon_r$ | $\sigma$ (S/m) |
|---|---|---|
| Skin | 35 | 0.6 |
| Muscle | 58 | 1.4 |
| Fat | 6 | 0.08 |
| Spinal cord | 49 | 1.1 |
| Blood | 62 | 1.5 |
| Cartilage | 35 | 0.6 |

The novel antenna unit described above preferably utilizes miniature antenna elements. For example, the maximal size of the conducting element of the antenna is significantly smaller than the wavelength for which the antenna is designed. Thus, it reduces substantially the form factor of the antenna and therefore, reduces the burden of carrying it. Moreover, the miniature size of the conductive elements allows it to be transplanted in an animate body in general and in a human body in particular.

The conductive elements may be of any suitable shape, such as but not limited to a ring shape (e.g. conductive pad) or of a line shapes (e.g. conductive wire).

In some applications of the invention, the antenna unit is used with a medical device. The antenna receives external electromagnetic radiation from the surroundings and produces a corresponding output electric signal for operating the medical device.

It should be noted that although in the above described examples the novel antenna unit of the present invention is shown as being used in electromagnetic harvesting systems to provide an improved intake of energy from the surroundings, this antenna unit may be utilized in communication systems for transmitting and receiving data, as well as medical applications for communication, for example, for data/signal exchange between an implanted medical device and an external element/system.

In a specific but not limiting example of the invention, the novel antenna unit may be implanted in and/or attached to a human body being used along with a medical device such as a pacemaker, a cardiac defibrillator, a hearing aid, an orthopedic electrical pulse producing device, and any other electric device that may be implanted in or attached to an animate body.

Figure 2:
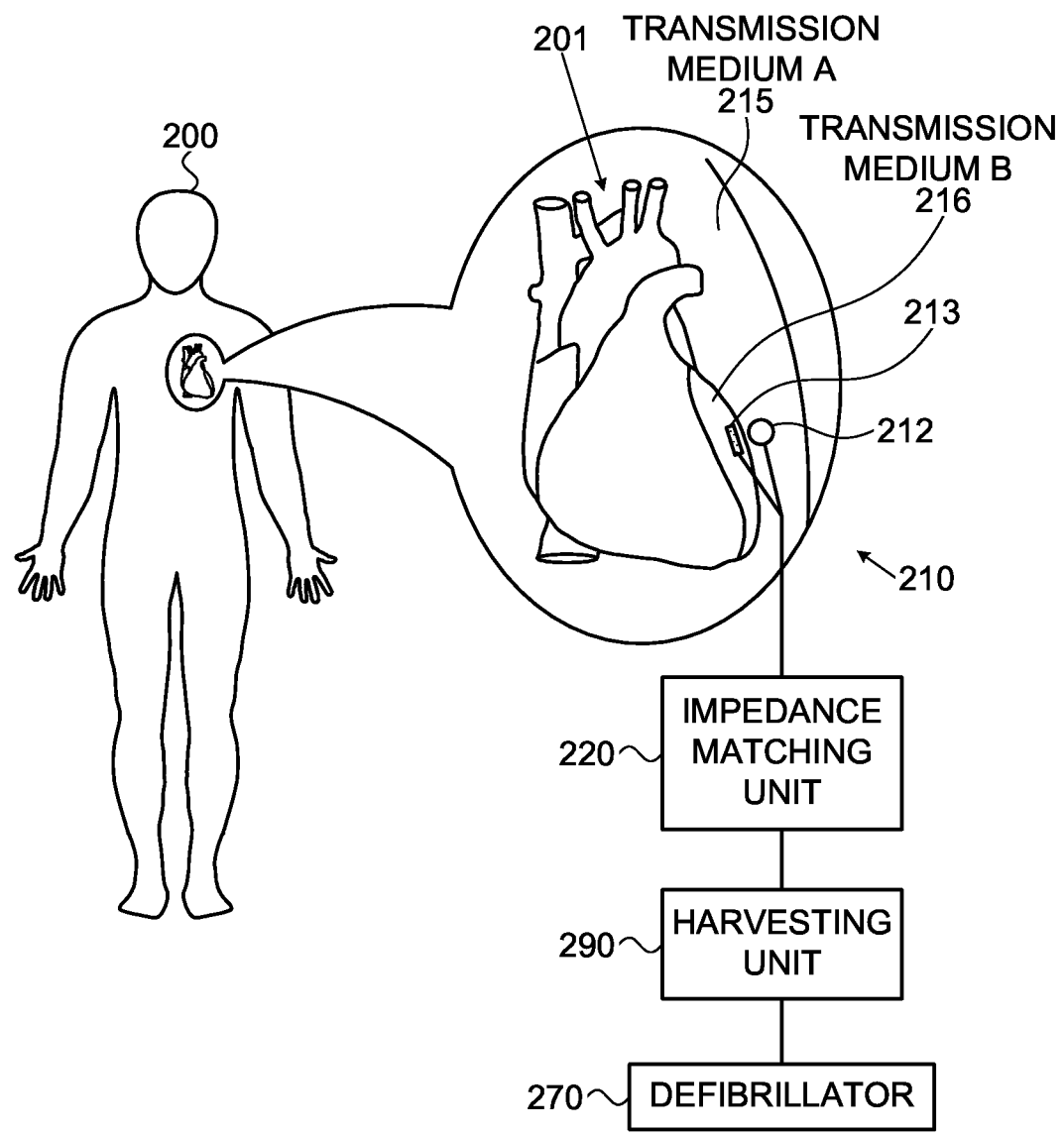
FIG. 2 is a schematic illustration of an example of an antenna unit of the present invention, being used with a heart pacemaker device implanted into a human body.

In this connection, reference is made to FIG. 2 that schematically illustrates the use of the system of the invention with an implanted medical device, where the antenna unit 210 is connected to an internal organ in the human body 200. In this example, the antenna unit 210 is implanted in a heart 201 of a human body 200 and a harvesting unit 90 is associated with (integral in or connected to) a defibrillator 270. Conductive elements 212 and 213 of the antenna unit 210 are imbedded in two different transmission media 215 and 216 respectively, which may, for example, be a fat layer surrounding the heart and a heart muscle. Due to the difference in the electrical properties of these two media 215 and 216, they differently interact with RF radiation in the surrounding and consequently different electric potentials are obtained in the substances and accordingly on the conductors 212 and 213 thereby creating an antenna effect and transmitting the electromagnetic radiation from the surrounding to the harvesting unit 290. Although in the illustration in the figure an input signal adapting unit is shown as a separate unit connected to the harvesting unit 290, it should be understood that such an input signal adapting circuit may be integral with the harvesting unit as shown in the non limiting examples of FIGS. 1A-1D. Also, it should be noted that although in this example, the input signal adapting unit is referred to as an impedance matching unit 220, the input signal adapting unit, as well as the entire harvesting unit (receiver) 290 may be configured and operable according to any of the above-described examples of FIGS. 1A-1D. Alternatively, as mentioned above, the system may utilize the novel antenna unit of the invention connected to any known suitable energy harvesting device having any known suitable impedance matching circuit. Thus, the antenna unit 210 is connected via the harvesting unit 290 to the defibrillator 270. It should be clear that all circuits and devices described in this figure are drawn schematically to emphasize the overall configuration.

Figure 3:
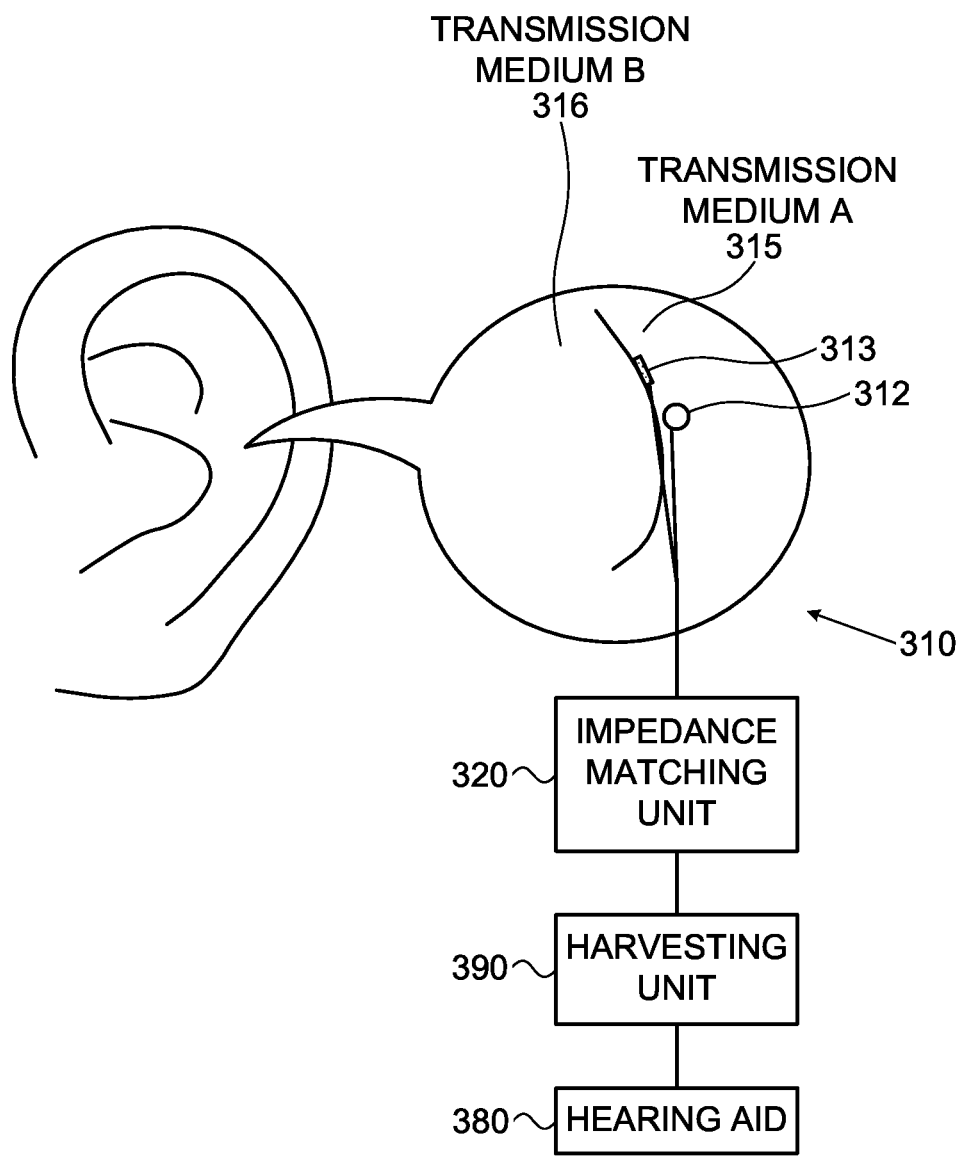
FIG. 3 is a schematic illustration of another example of the antenna unit of the invention being used with a hearing aid inserted into an individual's ear.

Reference is made to FIG. 3 that schematically illustrates how the present invention can be used in another medical application. Here, the system of the invention is associated with a hearing aid 380. As shown in the figure, an antenna unit 310 is attached to an ear 300 such that a conductive element 312 of the antenna unit is held in air (constituting a transmission medium 315), while a conductive element 313 is by its one end attached to ear 300 (constituting a different transmission medium 316). The conductive elements 312 and 313 by their free ends are connected to a harvesting unit 390; in the present not limiting example, the connection is via a separate input signal adapting unit, which has an impedance matching circuit 320. The output of harvesting unit 390 (e.g. its storage unit) that is connected to the hearing aid 380. All circuits and devices are drawn schematically to emphasize the overall configuration. As mentioned above, it should be understood that the harvesting unit together with impedance matching circuit may have any known suitable configuration, but preferably is configured as exemplified above with reference to FIGS. 1A-1D.

Figure 4A:
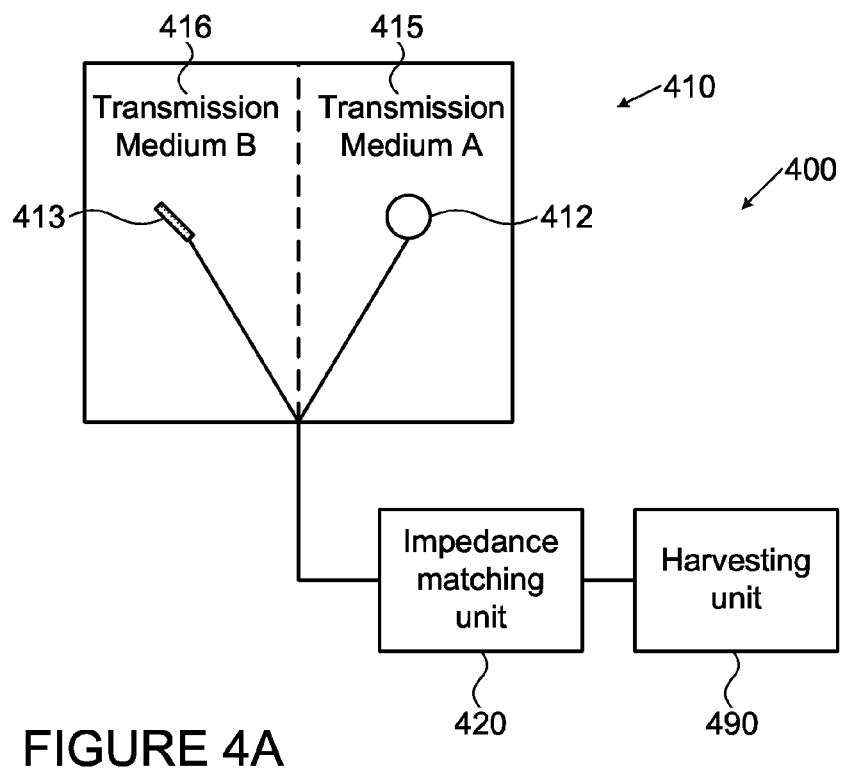
FIGS. 4A-4B are block diagrams schematically illustrating an example of a two-elements antenna system of the invention configured and operable for receiving energy from the surrounding (FIG. 4A), or connected to a transmitting unit (FIG. 4B).
Figure 4B:
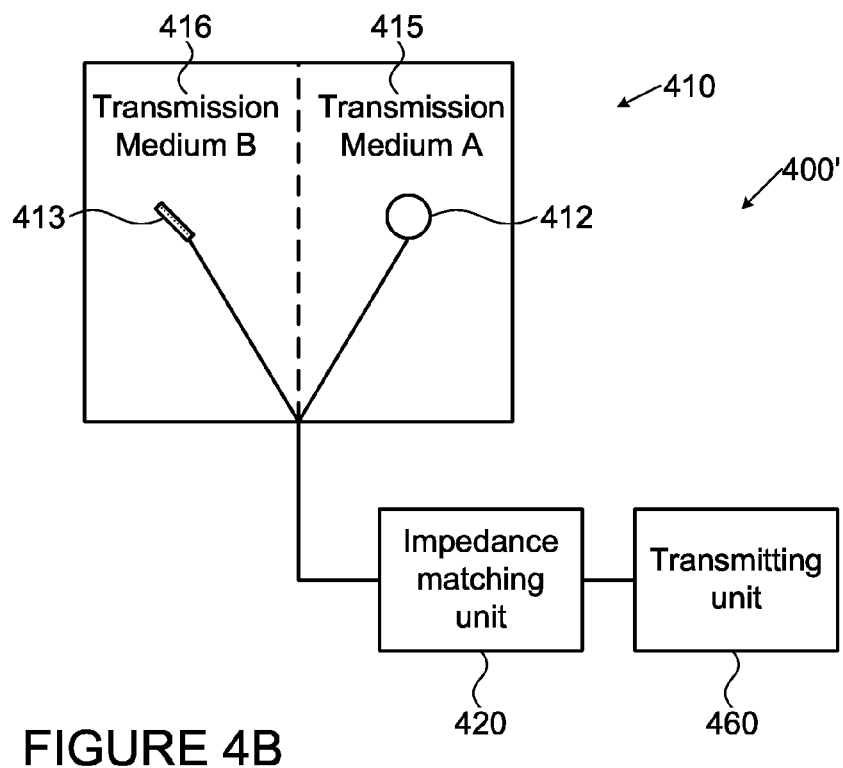

Reference is now made to FIGS. 4A and 4B that illustrate two examples of antenna systems of the present invention denoted 400 and 400' respectively. The systems are configured as a two-element receiving antenna, in which the antenna unit 410 includes conductive elements 412 and 413 embedded in different transmission media 415 and 416 respectively. In these specific non-limiting examples, the conductive element 412 has a closed-loop configuration or is a ring-like element (e.g. termed "conductive pad"), while conductive element 413 is a substantially straight strip-like element (e.g. termed "conductive wire"). It should be understood that the conductive elements may have any shape/geometry, e.g. both may be in the form of conductive pads or conductive wires.

In the example of FIG. 4A, conductive elements 412 and 413 are connected via an impedance matching unit/circuit 420 to a harvesting unit 490 (e.g. configured according to the invention as described above, or any other energy collection unit) the output of which may be further connected to an electrical load (not shown). In the example of FIG. 4B, the conductive elements 412 and 413 are connected through an impedance matching unit/circuit 420 to a transmitting unit 460 configured for transmission of data.

Figure 5:
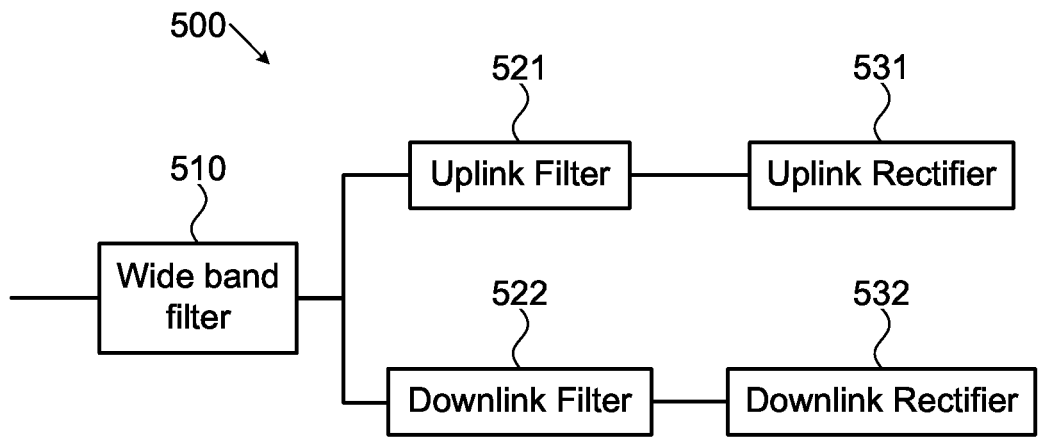
FIG. 5 is a schematic block diagram illustration of a filtering unit configured for maximizing the efficiency in an RF harvesting system.

The impedance matching unit 420 may include an adaptive impedance matching circuit as exemplified with reference to FIGS. 1B and 1C, or alternatively may include an impedance matching circuit connected to a filtering unit as exemplified in general above with reference to FIGS. 1A and 1D and will now be described more specifically with reference to FIG. 5.

The present invention, in its another aspect, provides a novel input signal adapting unit configured for maximizing the efficiency of the energy collection system. To this end, the input signal adapting unit is configured as a dedicated passive impedance matching filtering circuit formed by an impedance matching unit/module and a filtering unit/module. The configuration and operation of the filtering unit is based on the fact that in an RF harvesting system from the environment, the frequency and intensity (strength) of most harvested signals can be predefined, i.e. are either known a priori or are predictable, and therefore by using frequency filtering one can actually differentiate/sort the received signal for different intensities (strengths).

For example, there are typically two major categories of signals expected in be input signals for an RF harvesting system from the environment, both originated from the mobile phone RF system. The first is the signal from the base station to the cellular phone (downlink) and the second is the signal from the cellular phone to the base station (uplink) The downlink signal is characterized by a relatively low level signal and a different frequency than the uplink signal having a higher intensity. RF radio signals are also expected to be with the same frequency and intensity characteristics of as the downlink signals.

The filtering unit may include a preliminary wide band pass filter circuit with a wide enough frequency band to include both uplink and downlink frequency bands, and two or more narrow band filter circuits (defining at least one pair of such narrow band filters), one or more of them configured for the uplink frequency band(s) and one or more other of them configured for the downlink frequency band(s). The first wide band filter is responsible for receiving RF signal from the harvesting antenna and allowing passage of signals of both uplink and downlink frequencies. Each narrow band filters is responsible for allowing passage of AC signals in the appropriate frequency band, and accordingly in the appropriate corresponding intensity, to a dedicated rectifier so as to match the impedance of the rectifier according to the expected input intensity. The narrow band filters may be operable in parallel so as to simultaneously allow passage of AC signals in different narrow frequency bands.

It is understood that in different geographic locations, the expected frequency range and expected intensity may be different, and therefore the selection of the wide band filter and the narrow band filters may vary from country to country and from region to region and/or the filter circuit may include more than one pair (e.g. a large number of pairs) of filters to cover multiple combinations of the wide band filter and the narrow band filters.

It is understood that change in mobile (cellular) technology and/or mobile (cellular) transmission protocols may define various frequency bands that will be available for harvesting from the environment. However, due to ability of predicting their frequency and intensity, a dedicated narrow band filter and a corresponding rectifier can be designed.

It should be understood that the cellular uplink and downlink RF signals discussed above are only examples of available RF signals in the air, and other signals are within the scope of the present invention. The above aspect of the invention is exemplified in FIG. 5 which is a schematic block diagram illustration of a filtering unit 500 of the invention for maximizing the efficacy in an RF harvesting system. The filtering unit 500 includes a wide band filter 510 having an input that may receive an alternating current radiofrequency signal from a harvesting system antenna (not shown), and an output which is connected to narrow band filters—two such filters 521 and 522 being shown in the example of FIG. 5. Narrow band filter 521 is designed to allow passage of signals in the uplink frequency range of the cellular system and is connected in parallel to the narrow band filter 522, which is designed to allow passage of signals in the downlink frequency range of the cellular system. Wide band filter 510 is configured for passing both of the uplink and the downlink frequency bands.

Narrow band filter 521 is connected to a dedicated rectifier 531 designed for receiving signals of an expected strength, and narrow band filter 522 is connected to another dedicated rectifier 532 that is similarly designed for optimally obtaining signals of the expected frequency and strength from filter 522. The impedance of each of the rectifiers 531 and 532 is matched according to the expected intensity parameters (strength) in the specific frequency band, originated from the RF system.

For realization of the exemplary filtering unit described above, a numeric example is herein provided: A radiation band having a central frequency of 1 GHz and bandwidth (BW) of 800 MHz is received by the antenna. This band contains desired frequencies that need to be harvest. The frequencies in accordance with this specific example are 915 MHz and 950 MHz. The received band is transferred from the antenna to the first wide band filter that allows transmission of a 60 MHz band centered at 930 MHz. The received signals obtained from the first filter are thus between the frequencies of 900 MHz to 960 MHz. The parallel second and third narrow band filters are now receiving signals between 900 MHz to 960 MHz, while the second filter is set to center frequency 915 MHz with BW of 30 MHz and the third filter is set to center frequency of 945 MHz with BW of 30 MHz. The received signals' strength in the band of 915 MHz are predicted to be in the range of (−30) dbm to (−20) dbm, and the received signals strength in the band of 950 MHz are predicted to be in the range of (−5) dbm to 5 dbm.

The rectifier unit connected to the filtering unit includes a corresponding number of rectifiers, the rectifier connected to the second band pass filter is matched to rectify signal strength in the range between (−30) dbm to (−20) dbm and the rectifier connected to the third band pass filter is matched to rectify signal strength in the range between (−5) dbm to 5 dbm.

It should be understood that the invention is neither limited to a number of filters in the filtering unit described above, nor to any specific frequency bands. Additional signals propagating in the surroundings of the antenna and suitable to be used by such filtering circuit, include those having the priori known frequency and strength of a commercial radio channel. The expected signal strength received from a commercial radio channel is from (−50) dbm to −40 dbm. In this case, the filter may be set for the channel frequency and the corresponding rectifier may be matched to a strength range of (−50) to (−40) dbm. In case of parallel radio channels, for example, between 88 MHz and 108 MHz, the receiver (e.g. harvesting unit) can be matched to the strength of the entire band received from the band pass filter.

The present invention in its yet further aspect provides a novel charge collecting unit suitable to be used in the energy harvesting system. The charge collecting unit of the present invention is configured as a signal summing utility adapted for accumulating charge from relatively small capacitor units to a large capacitor unit.

In some embodiments of the invention, such signal summing utility is configured to appropriately accumulate charge mainly by changing the topology of various components of the unit. In this case, the summing utility may include such functional modules/circuits as a relatively small storage charging circuit, and a switching circuit, connected to a relatively large storage charging circuit (which may be that of the storage unit in the harvesting system).

The small storage charging circuit includes a plurality of capacitor units. The small storage charging circuit may for example be adapted for accumulating charge obtained from the output of the rectifying unit (i.e. plurality of rectifiers) and for storing the charge created on multiple capacitor units. Each of the capacitor units in the small storage charging circuit may include a plurality of capacitors being in serial and/or parallel connections.

The switching circuit may be adapted for determining the mode of the circuit, defining the function thereof as a charging function or as a discharging function. The discharging of the small storage charging circuit may be performed simultaneous or single charging unit at a time, or according to predetermined time pattern for multiple storage charging units. The plurality of switches in the switching circuit may be operated independently, as well as may be connected and switched (operated) according to a predetermined switching pattern, for example a certain switch is activated depending on the operative state of the locally adjacent switches. The plurality of switches in the switching circuit may be controllably operated as exemplified above with reference to FIGS. 1B and 1D.

The charge collection unit of the present invention may be designed to be associated with a plurality of harvesting units. Each harvesting unit may capture RF energy, rectify and store the energy as a charge on a capacitor unit. In some embodiments of the present invention, the plurality of harvesting units may capture plurality of frequency bands, wherein each harvesting unit may be adapted to capture a specific frequency band. Additionally or alternatively, at least two harvesting units may be adapted to capture similar frequency band.

The large storage charging circuit may be adapted for accumulating and storing the charge pre-stored in each of the plurality of small capacitor units in a large storage charging unit for further usage. The large storage charging circuit may include a plurality of capacitors in serial and/or parallel connections. The output of the large storage charging circuit may for example be followed by one or more of the following: a step up convertor; a voltage stabilizer; a battery charging circuit; a capacitor array, an electrical load. In some embodiments, the output of the large storage charging subunit may be either switched or constantly short to the circuit.

Some examples of various switching options are provided below with reference to FIGS. 6-10.

Figure 6:
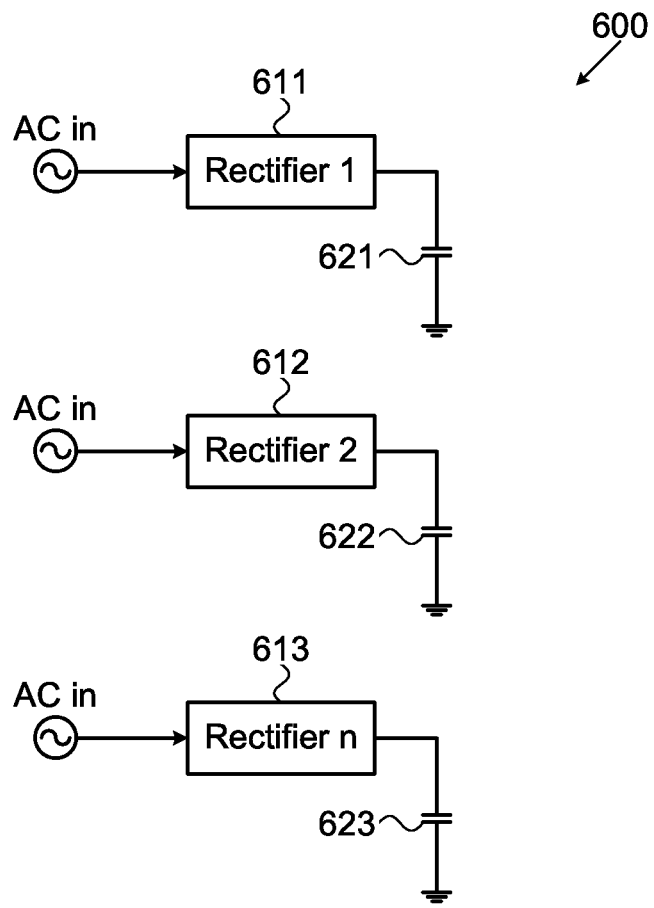
FIG. 6 is a schematic block diagram illustration of a standard circuit for charging capacitors from rectifying elements.

FIG. 6 is a schematic block diagram illustrating a standard charge collection circuit 600 that might be used in the energy harvesting system of the invention. The collection circuit 600 includes a plurality of charging capacitor units—three such units 621, 622, and 623 being shown in this non-limiting example. In this example, the charge collection circuit 600 operates for collecting charge from a rectifying unit including a plurality of rectifier elements—three such elements 611, 612 and 613 being shown in this non-limiting example. Each charging capacitor unit is connected to a corresponding one of the rectifier elements and connected to ground. Each of the rectifiers 611, 612 and 613 receives AC signal from a harvesting antenna unit or from any other element positioned between the antenna unit and the rectifier (e.g. input signal adapting unit, e.g. impedance adaptor), rectifies the signal, and the corresponding energy is stored as electric charge in the corresponding one of the capacitor unit 621, 622, and 623. It is understood that each capacitor unit may be configured as a single capacitor unit or multi-capacitor unit where the multiple capacitors may be connected in any serial and/or parallel connections. It is understood also that each rectifier element may receive AC signal in a similar or different frequency band. It should be noted that the circuit 600 is neither limited to a specific number of rectifier-capacitor arrangements nor to a specific electrical connection of the capacitors, and FIG. 6 is just an example of the operational principles of the charge collection unit.

Figure 7:
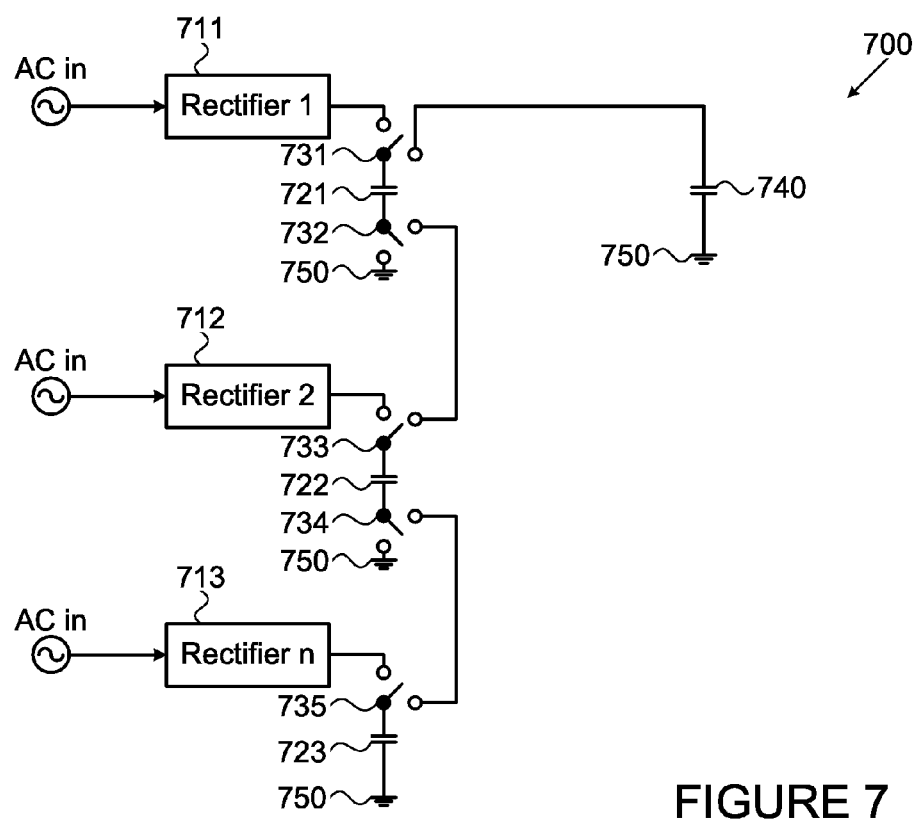
FIG. 7 is a schematic block diagram illustration of a system for accumulating charge from small capacitors to a large capacitor.

Reference is now made to FIG. 7 which is a schematic block diagram illustration of a charge collection unit 700 configured and operable according to the present invention. The charge collection unit 700 is operable as a signal summing unit, and includes a plurality of small capacitor units—thee such units 721, 722 and 723 being shown in this non-limiting example. The capacitor units 721, 722 and 723 are at one ends connected via switching circuits to rectifiers 711, 712 and 713 respectively, and at the other ends are connected to ground 750. Also provided in the charge collection unit 700 is a large capacitor unit 740 which is connected to the capacitor units 721, 722 and 723 via the switching circuits. The switching circuits include a plurality of switches 731, 732, 733, 734 and 735, each configured with two working/operative positions 1 and 2. The distribution of switches positions between positions 1 and 2 determine the functionality of the switching circuit, as will be described with reference to FIGS. 8 and 9. As shown in the figure, the switches 731, 733 and 735 selectively connects the charge collection unit 700 to the rectifying unit.

Thus, each rectifier receives AC signal from a harvesting antenna or from any other intermediate circuit communicating the antenna signal to the rectifier. The energy rectified by each of the multiple rectifiers of the rectifying unit is being stored as electric charge in the corresponding capacitor unit of the charge collection unit 700. As shown in the figure in a self-explanatory manner, each capacitor unit is on its other end selectively connectable either to ground 750 or to the large capacitor unit 740 through the corresponding two-state switches, and on its other end is selectively connectable either to the respective rectifier or to the large capacitor unit 740 through the other two-state switches.

The charge collection unit operates in the following manner. The switches 731-735 are controlled by the controller, which can turn them to any given mode (charging/discharging) based on real time monitoring of each of the capacitors 721-723 connected to the outputs of the rectifiers. Based on the information (voltage level) received from each capacitor, the controller can determined as to whether to keep the circuit in the charging mode or whether it is ready to discharge into the storage capacitor. The received information from the capacitors 721-723 can also be indicative of whether the harvesting process is ongoing, and whether the reached voltage level is maximal at the time. Based on this information, the controller turns the switches into charging or discharging mode.

Further, the controller can define a full discharge mode (when all the capacitors are discharged together), semi discharge mode (only some of the capacitors are discharged while the others remain in charging mode), and charging mode (all capacitors are being charged).

Another option for the controller operation is based on a programmable pattern (i.e. predefined values). When the voltage of the capacitor 721-723 reaches a certain voltage level (as being defined), the switches are turned to the discharge mode. When the discharge is complete (can be defined as well), the switches are being turned back into the charging mode. This method allows three modes: full discharging, semi discharging and full charging.

It is understood that each of capacitor units 721, 722, and 723 may be configured as a single capacitor unit or as a multi-capacitor unit in which an array of capacitors are connected in some combination of serial and parallel connections. Similarly, that the large capacitor unit 740 may have a single-capacitor configuration or may be a multi-capacitor circuit utilizing a proper serial and/or parallel connection between the capacitors.

It should be understood that the configuration exemplified herein is neither limited to a number of rectifiers in the rectifying unit nor to a number of small capacity units in the charge collection unit 700. It should also be clear that all circuits and devices described in this figure are drawn schematically to emphasize the overall configuration.

Figure 8:
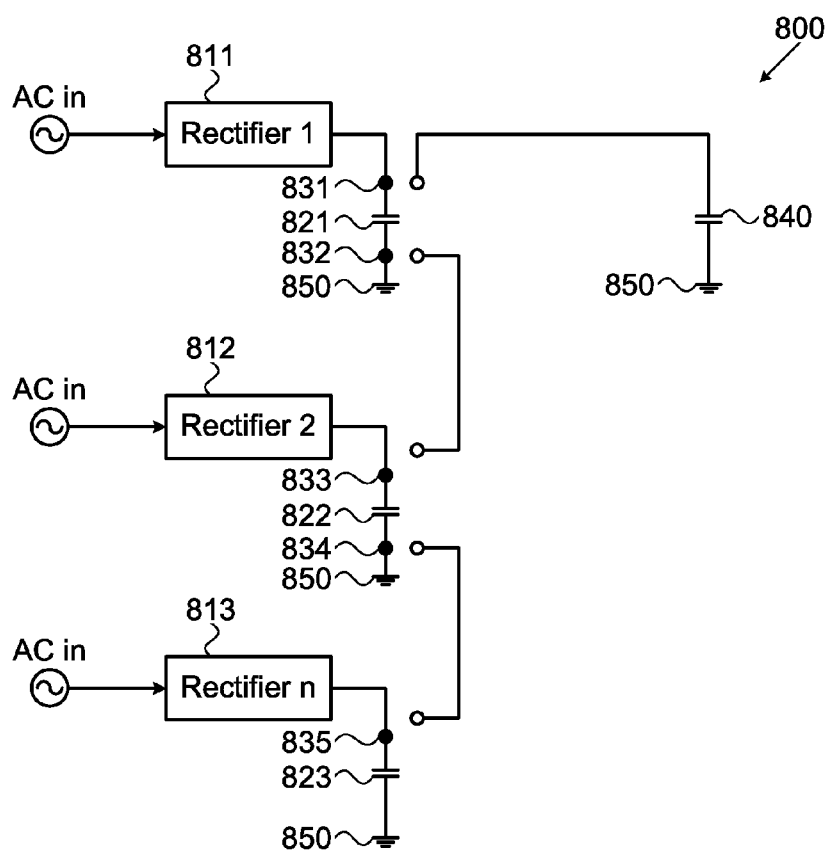
FIG. 8 is a schematic block diagram illustration of a system for accumulating charge from small capacitors to a large capacitor in a charging switches position.
Figure 9:
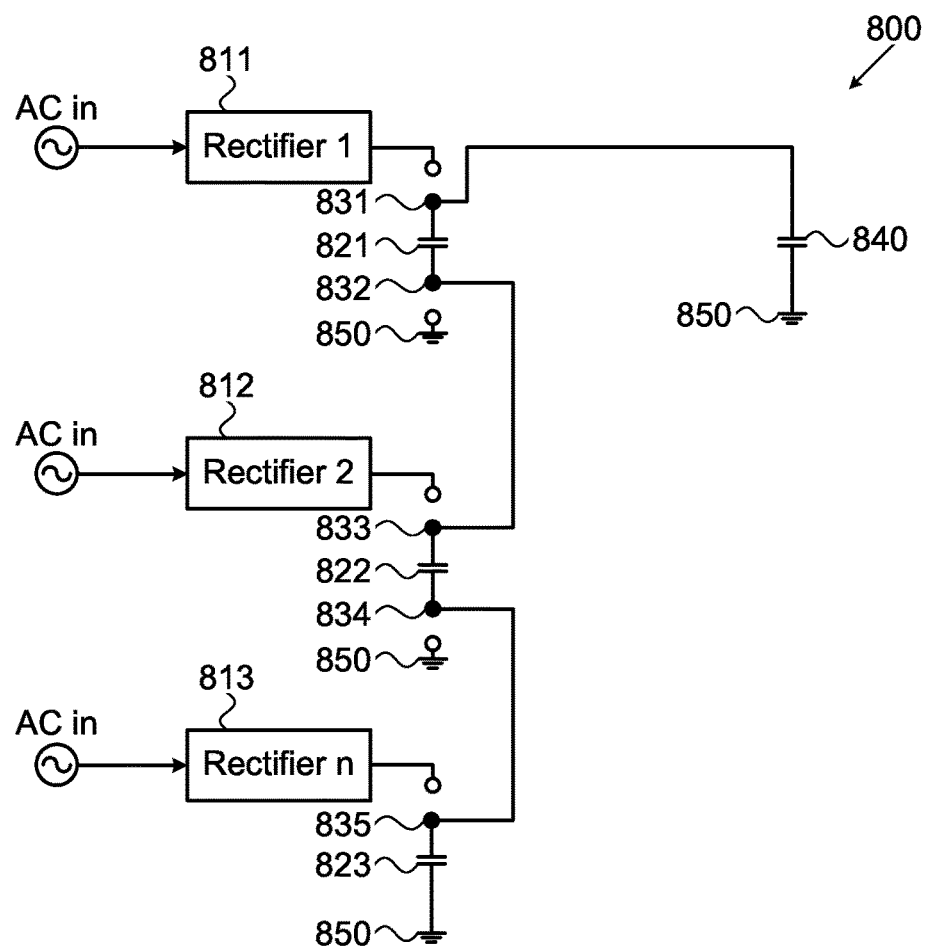
FIG. 9 is a schematic block diagram illustration of a system for accumulating charge from small capacitors to a large capacitor in a discharging switches position.

FIGS. 8 and 9 schematically illustrate another example of a charge collection or signal summing unit 800 of the invention. The charge collection unit 800 is configured generally similar to the above described unit 700, namely includes multiple small capacitor units denoted as 821, 822 and 823 connected to multiple rectifiers 811, 812, 813, respectively, of a rectifying unit, and connectable to a large capacitor unit 840 in a charging configuration via switching circuit including multiple switches 831, 832, 833, 934 and 835. The capacitor units 821, 822 and 823 are at one ends connected to the rectifiers, and at the other ends are connected to ground 850.

As mentioned above, the small capacitor units 821, 822, and 823 as well as large capacitor unit 840 may include single-capacitor configuration(s) or multi-capacitor configuration(s) connected to one another in serial and/or parallel connections. Also, the invention is not limited to a number of rectifiers in the rectifying unit; the number of small capacity units is selected in accordance with the number of the rectifiers. Further, as also mentioned above, all circuits and devices described in this figure are drawn schematically to emphasize the overall configuration.

The configuration 800 is different from the above-described example of FIG. 7 in a somewhat different configuration of switching elements 831, 832, 833, 834 and 835. Each of the switches 831, 833, 835 selectively connects the respective capacitor unit to the corresponding rectifier or to the large capacitor unit 840, and the other switches selectively connect the respective capacitor units to ground 850 or to the large capacitor unit 840.

FIG. 8 shows the switching configuration of the summing unit 800 corresponding to a charging configuration. Each capacitor unit is connected directly to its corresponding rectifier and is being charged. It is understood that capacitor units 821, 822 and 823 may be charged in different charges.

FIG. 9 shows the signal summing unit 800 of FIG. 8 in a discharging configuration. As shown, the switching elements 831, 832, 833, 834 and 835 are in a switch position topology connecting each of small capacitor units 821, 822 and 823 to the large capacitor unit 840. In this discharging configuration all small capacitor units 821, 822 and 823 are connected in series and their resultant capacitor is connected in parallel to the large capacitor unit 840, i.e. electrical charge is being transferred from small capacitor units 821, 822, and 823 to large capacitor unit 840. The change of the switching state from the topology described in FIG. 8 to the topology described in FIG. 9 results in charge transfer from small capacitor units 821, 822 and 823 to large capacitor unit 840. Since the voltage across the small capacitor units is higher than the voltage across the large capacitor unit 840, the flow of charge is directed from small capacitor units to large capacitor unit until equilibrium is reached.

Figure 10:
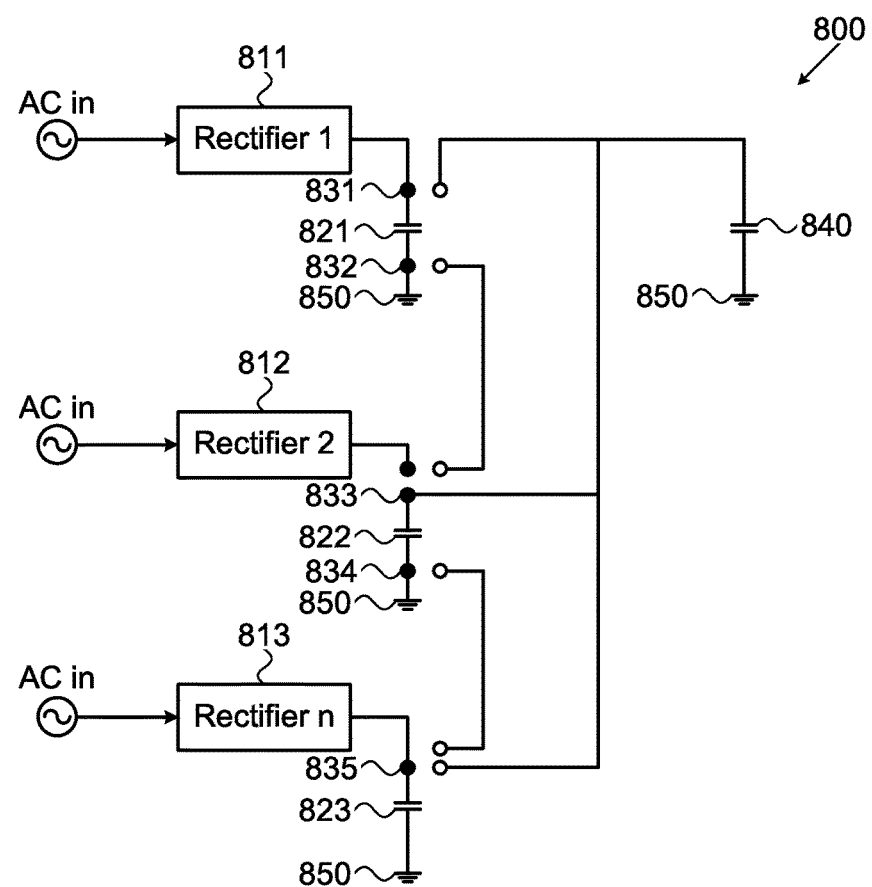
FIG. 10 is a schematic block diagram illustration of a system for accumulating charge from small capacitors to a large capacitor in a single discharging switch position.

FIG. 10 exemplifies a signal summing unit 800 of FIGS. 8-9 modified to have a single discharging configuration. In the scenario illustrated in this figure, switching elements 831, 832, and 835 are in a switch position topology connecting small capacitor units 821, and 823 to rectifiers 811 and 813 respectively on one side, and to ground 850 on the other side, while being disconnected from the large capacitor unit 840. This switching configuration is a charging configuration of capacitors 821 and 823 from rectifiers 811 and 813 respectively associated with harvesting unit/units. However, switching elements 833 and 834 are positioned in a topology that allows for connecting small capacitor unit 822 to the large capacitor unit 840 in a parallel configuration, i.e., in a discharging position. In other words, in the scenario illustrated in FIG. 10, one or more of the capacitor units may be discharged while one or more other capacitor units remain charged: small capacitor unit 822 may be discharged to large capacitor unit 840 while the other capacitor units 821 and 823 remain charged.

In accordance with the example of FIG. 10, switching elements 833 and 835 are configured with three optional positions, each changing the topology of the circuit and its functionality. These switching elements, when being in the first operational state/position, connect the small capacitor units 822 and 823 to respective rectifiers 812 and 813 thus allowing charging of capacitor units 822 and 823. When in the second operational position of switching elements 833 and 835 they create serial connection of the small capacitor units 821, 822 and 823 to thereby allow simultaneous discharge of the small capacitor units to the large capacitor unit 840. The third operational position of these switching elements allows direct discharge of the small capacitor unit 822 or 823 to the large capacitor unit 840. It should be understood that the small capacitor unit 821 might be capable of being discharged autonomously, directly to the large capacitor unit 840.

As indicated above, this embodiment of the summing unit is also not limited to any specific number of small capacitor units, and this number corresponds to a number of rectifiers in a rectifying unit, and that all circuits and devices described in this figure are drawn schematically to emphasize the overall configuration.

As described above with reference to FIGS. 1A and 1C, in some embodiments of the invention the charge collection unit or signal summing unit allows accumulation of charge in the harvesting system by converting the electric voltage developed on capacitors, connected to the outputs of rectifiers, into electric current source. In such variation, the summing unit includes a small storage charging utility/circuit, a voltage to current converter utility/circuit; and a large storage charging utility/circuit.

The small storage charging circuit might be mainly adapted for storing the charge obtained via the plurality of rectifiers by using a plurality of capacitor units as described above. The voltage to current converter circuit may be configured for converting, upon reaching a threshold, the voltage, developed in the small storage charging utility, into current, to be delivered to a large storage charging utility. The large storage charging utility may be configured for accumulating and storing the current arriving from voltage to current conversion in the form of charge in a large storage charging unit for further usage.

In some embodiments of the present invention, the small storage charging circuit may be designed as a plurality of harvesting units. Each harvesting unit may capture RF energy, rectify and store the energy as a charge on a capacitor unit.

The plurality of harvesting units may capture plurality of frequency bands, wherein each harvesting unit may be adapted to capture a specific frequency band, or at least two harvesting units may be adapted to capture similar frequency bands different from that/those of other harvesting units.

The plurality of harvesting circuits may have plurality of capacitor values. In some embodiments, each capacitor unit in the plurality of capacitor units in the small storage charging circuit may include a plurality of capacitors in serial and/or parallel connections (capacitors array).

The discharging of the small storage charging units may be performed by converting the voltage developed on each of the capacitor units in the plurality of capacitor units to an electric current, by using a voltage to current converter units. The multiple voltage to current converter units of the voltage to current converter circuit may be operable independently; and/or may be operable by a controller that controls all voltage to current converter units or parts thereof. The voltage to current converter units may have voltage thresholds, defining the minimal voltage triggering the conversion of voltage to current. The voltage thresholds of the voltage to current converter units may be different; as well as may be changed by the controller.

Multiple voltage to current converter units may operate substantially simultaneously, as each unit operates independently and do not interfere to the current converted by other units.

Each voltage to current converter unit may restrict current flow backwards from the large storage charging circuit to the small storage charging circuit, as the voltage to current converter has the ability to force flow of charge in a certain direction.

The large storage charging circuit may include a plurality of capacitors in serial and/or parallel connections. In some embodiments, the output of the large storage charging circuit may be connected to one or more of the following: a step up converter; a voltage stabilizer; a battery charging circuit; a capacitor array, and an electric load. In some embodiments, the output of the large storage charging circuit may be either switched or constantly short to the circuit.

Figure 11:
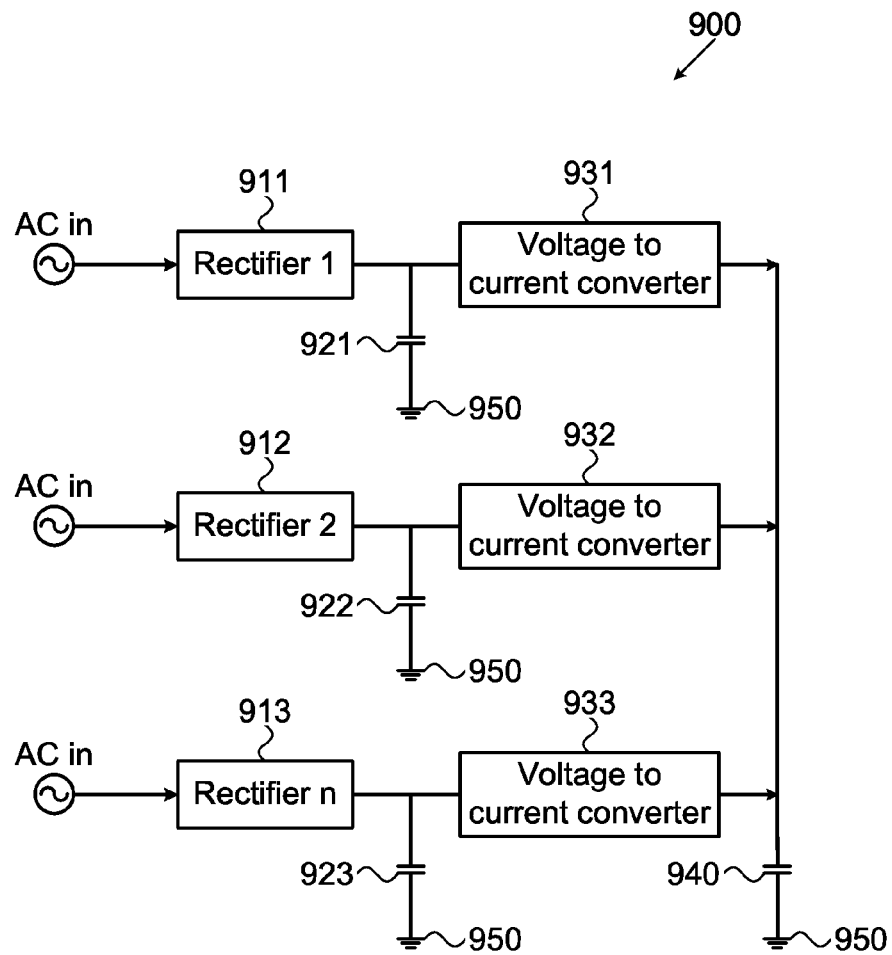
FIG. 11 is a schematic block diagram illustration of a system for accumulating charge from small capacitors to a large capacitor by converting the stored electric charge to electric current source.

FIG. 11 schematically illustrates an example of a charge collection unit or signal summing unit 900 for accumulating charge corresponding to output of a plurality of rectifiers 911, 912, 913 of a rectifying utility of a harvesting system. The signal summing unit 900 includes a small capacitor circuit which in the present example is formed by small capacitor units designated as 921, 922 and 923; a voltage to current convertor circuit which in this example is formed by a plurality of voltage to current converters 931, 932 and 933; and a large capacitor unit/circuit 940. The small capacitor units 921, 922 and 923 are at one end connected to the rectifiers 911, 912 and 913 respectively and to the voltage to current converters 931, 932 and 933, and on the other end are connected to ground 950.

Each rectifier receives AC signal from a harvesting antenna unit (or from any other intermediate utility positioned between the antenna unit and the rectifiers), and rectifies the signal. Each of the rectifiers 911, 912 and 913 is also connected to the respective one of the voltage to current converters 931, 932 and 933. The charge of each of the rectifiers 911, 912 and 913 is being stored, up to a predetermined threshold, as an electric charge in the corresponding one of the small capacitor units 921, 922 and 923. Each of the voltage to current converters 931, 932 and 933 has an intrinsic voltage threshold value that switches the voltage to current converter from a disconnection position (inoperative state) to a connection position (operative state). In the disconnection position of one of the voltage to current converters 931, 932 and 933, all current from the corresponding rectifier flows to the corresponding small capacitor unit. Thus, the charge accumulation in the corresponding small capacitor unit increases the voltage on the corresponding small capacitor unit. When voltage threshold is reached, the corresponding voltage to current converter operates as a unidirectional connector, forcing the charge developed in the small capacitor unit to flow directly towards the large capacitor unit 940.

It is understood that each of small capacitor units 921, 922, and 923 as well as the large capacitor unit 940 may be configured as a single capacitor unit or may include an array of capacitors connected in some combination of serial and parallel connections. It should also be clear that any number of rectifiers may be used, and the number of small capacity units and the number of voltage to current converters is selected accordingly, and that all circuits and devices described in this figure are drawn schematically to emphasize the overall configuration.

The invention claimed is:

1. An antenna unit configured and operable for receiving external electromagnetic radiation from surroundings and producing a corresponding output electric signal, said antenna unit comprising at least two conductive elements positioned in at least two different transmission media being different substances that are different in at least one of electric and magnetic properties, such that received external electromagnetic radiation creates a potential difference between the at least two conductive elements producing an output electric signal, thereby allowing uptake of the external electromagnetic radiation from the surroundings.

2. The antenna unit according to claim 1, wherein said at least two different transmission media include different animate tissues.

3. The antenna unit according to claim 1, being attached to an animate body, wherein said at least two different transmission media include animate tissue and air.

4. The antenna unit according to claim 1, where said antenna is connected to transmitting unit and configured for transmitting electromagnetic radiation.

5. A system for harvesting electromagnetic energy propagating in surroundings, said system comprising:
the antenna unit of claim 1 configured for receiving external electromagnetic radiation from the surroundings and producing a corresponding electric output;
a harvesting unit for receiving signals indicative of the output of the antenna unit and generating and storing corresponding electric charge; and
an input signal adapting circuit being configured and operable for adjusting a predetermined electrical property of the antenna unit to optimize receipt of the electric output of the antenna unit to the harvesting unit.

6. The system according to claim 5, wherein said antenna unit comprises at least two conductive elements positioned in at least two different transmission media being different in at least one of electric and magnetic properties.

7. The system according to claim 6, wherein said at least two different transmission media include at least two different anima issues.

8. The system according to claim 6, wherein said at least two different transmission media include animate tissue and air.

* * * * *